United States Patent
Lewis et al.

(10) Patent No.: US 8,182,802 B2
(45) Date of Patent: *May 22, 2012

(54) COMPOSITION OF POLYMERS

(75) Inventors: Andrew Lennard Lewis, Surrey (GB);
Steven Peter Armes, Sheffield (GB)

(73) Assignee: Biocompatibles UK Limited, Farnham Surrey (GB)

( * ) Notice: Subject to any disclaimer, the term of this patent is extended or adjusted under 35 U.S.C. 154(b) by 1836 days.

This patent is subject to a terminal disclaimer.

(21) Appl. No.: 10/506,814

(22) PCT Filed: Mar. 7, 2003

(86) PCT No.: PCT/GB03/00992
§ 371 (c)(1),
(2), (4) Date: Jan. 19, 2005

(87) PCT Pub. No.: WO03/074090
PCT Pub. Date: Sep. 12, 2003

(65) Prior Publication Data
US 2005/0163743 A1    Jul. 28, 2005

(30) Foreign Application Priority Data
Mar. 7, 2002 (EP) .................................... 02251605

(51) Int. Cl.
*A61K 31/00* (2006.01)
*A61K 48/00* (2006.01)
*C12N 15/88* (2006.01)

(52) U.S. Cl. .................. 424/78.3; 424/78.17; 514/44 R; 435/458

(58) Field of Classification Search ................ 424/78.3; 514/44, 44 R; 435/458
See application file for complete search history.

(56) References Cited

U.S. PATENT DOCUMENTS

| | | | |
|---|---|---|---|
| 6,270,788 B1 * | 8/2001 | Koulik et al. ................. | 424/423 |
| 6,291,620 B1 * | 9/2001 | Moad et al. ................... | 526/319 |
| 6,310,175 B1 * | 10/2001 | Kobayashi et al. ........... | 528/374 |
| 6,440,743 B1 * | 8/2002 | Kabanov et al. .............. | 435/458 |
| 6,852,816 B2 | 2/2005 | Lewis et al. | |
| 7,300,990 B2 | 11/2007 | Lewis et al. | |

(Continued)

FOREIGN PATENT DOCUMENTS

WO       WO 95/05408 A1     2/1995

(Continued)

OTHER PUBLICATIONS

Bronich et al., "Effects of Block Length and Structure of Surfactant on Self-Assembly and Solution Behavior of Block Complexes," in Langmuir, 2000, vol. 16, 481-489).*

(Continued)

*Primary Examiner* — Blessing Fubara
(74) *Attorney, Agent, or Firm* — Sughrue Mion, PLLC

(57) ABSTRACT

Compositions are described comprising a of a block copolymer having an overall ionic charge and in which one of the blocks has pendant zwitterionic groups and a biologically active compound having a charge opposite that of the polymer. The polymer is preferably a linear diablock copolymer, preferably having a low polydispersity, such as a (tertiary amine group containing monomer) block-(zwitterionic monomer) copolymer. Suitable cationic monomers are dialkyl aminoalkyl(alk)acrylates and -acrylamides and suitable zwitterionic monomers are phosphorylcholine group containing acrylate monomers such as 2-methacyloyloxyetyl-$2^1$-trimethyl ammonium ethyl phosphate liner salt. The biologically active compound is generally polyionic and is for instance a nucleic acid, such as DNA, especially plasmid DNA.

30 Claims, 6 Drawing Sheets

U.S. PATENT DOCUMENTS

Figure 3:
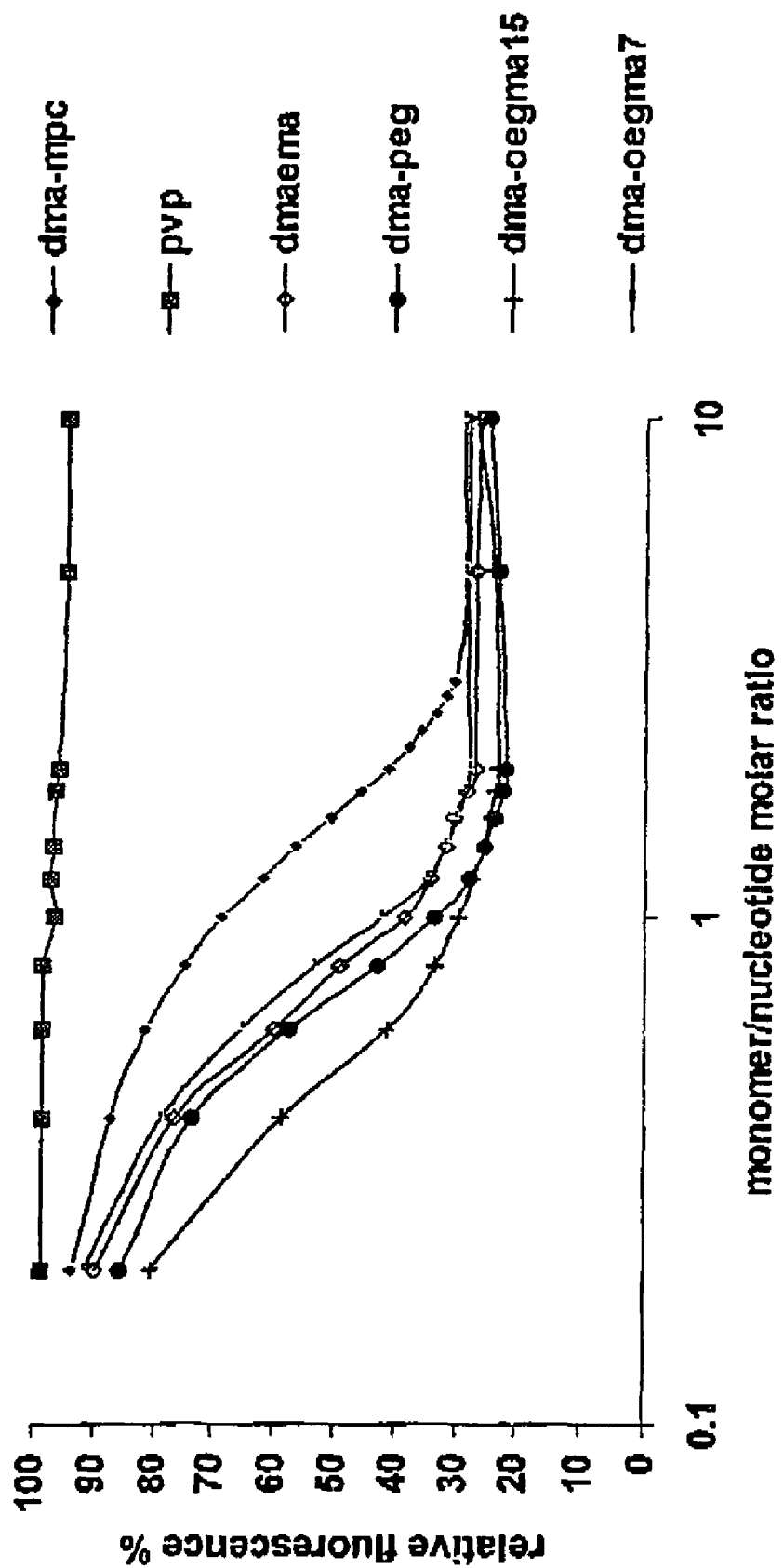

| | | |
|---|---|---|
| 2005/0123501 A1 | 6/2005 | Lewis |
| 2005/0220880 A1 | 10/2005 | Lewis |
| 2006/0069203 A1 | 3/2006 | Lewis |
| 2006/0135714 A1 | 6/2006 | Lewis |

FOREIGN PATENT DOCUMENTS

| | | | |
|---|---|---|---|
| WO | WO 98/22516 A1 | | 5/1998 |
| WO | WO 98/22517 | * | 5/1998 |
| WO | WO 98/22517 A1 | | 5/1998 |
| WO | WO 98/56334 A1 | | 12/1998 |
| WO | WO 98/56348 A1 | | 12/1998 |
| WO | WO 99/06055 A1 | | 2/1999 |
| WO | WO 00/28920 | * | 5/2000 |
| WO | WO 00/28920 A1 | | 5/2000 |
| WO | WO 00/29481 | * | 5/2000 |
| WO | WO 00/29481 A1 | | 5/2000 |
| WO | WO 01/27209 | * | 4/2001 |
| WO | WO 02/28929 | * | 4/2002 |

OTHER PUBLICATIONS

Georges et al., "Narrow molecular weight resins by a free-radical polymerization process," in Macromolecules, 1993, 26 (11), pp. 2987-2988.*

Chiefari et al., "Living Free-Radical Polymerization by Reversible Addition—Fragmentation Chain Transfer: The RAFT Process," in Macromolecules, 1998, 31 (16), pp. 5559-5562.*

V. Bütün et al., "Selective betainisation of tertiary amine methacrylate block copolymers", J. Mater. Chem., vol. 7, No. 9, (1997), pp. 1693-1695.

T.K. Bronich et al., "Effects of Block Length and Structure of Surfactant on Self-Assembly and Solution Behavior of Block Ionomer Complexes", Langmuir, vol. 16, (2000), pp. 482-489.

T. Govender et al., "Drug-polyionic block copolymer interactions for micelle formation: physicochemical characterisation", Journal of Controlled Release, vol. 75, (2001), pp. 249-258.

T. Inoue et al., "An AB block copolymer of oligo(methyl methacrylate) and poly(acrylic acid) for micellar delivery of hydrophobic drugs", Journal of Controlled Release, vol. 51, (1998), pp. 221-229.

A.L. Lewis et al., "Synthesis and characterisation of phosphorylcholine-based polymers useful for coating blood filtration devices", Biomaterials, vol. 21, (2000), pp. 1847-1859.

A.L. Lewis et al., "Crosslinkable coatings from phosphorylcholine-based polymers", Biomaterials, vol. 22, (2001), pp. 99-111.

U. Rungsardthong et al., "Copolymers of amine methacrylate with poly(ethylene glycol) as vectors for gene therapy", Journal of Controlled Release, vol. 73, (2001), pp. 359-380.

D.A. Styrkas et al., "pH-Controlled Adsorption of Polyelectrolyte Diblock Copolymers at the Solid/Liquid Interface", Langmuir, vol. 16, (2000), pp. 5980-5986.

M. Vamvakaki et al., "Synthesis of Controlled Structure Water-Soluble Diblock Copolymers via Oxyanionic Polymerization", Macromolecules, vol. 32, (1999), pp. 2088-2090.

* cited by examiner

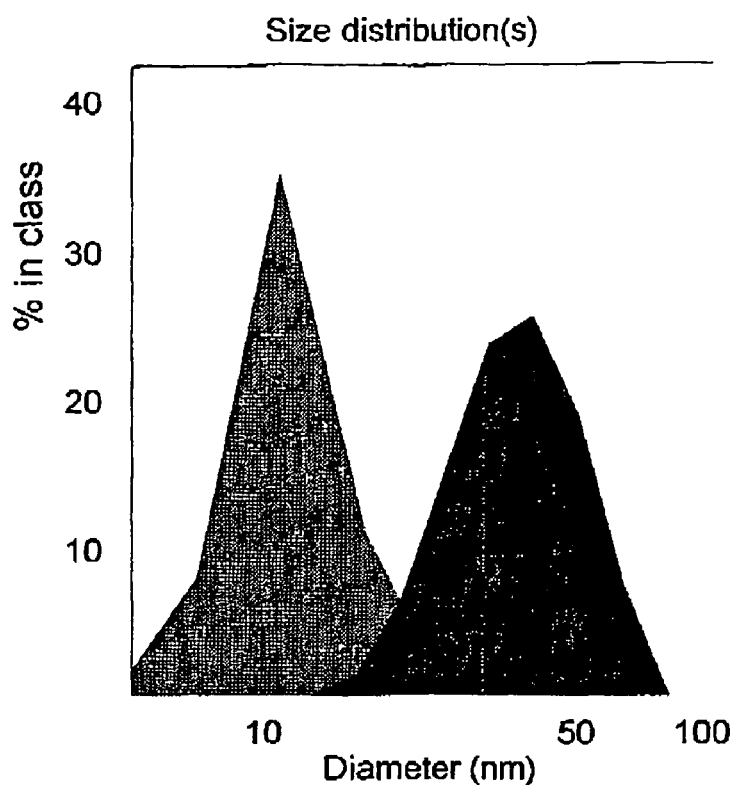
Figure 1. Paricle size (nm)
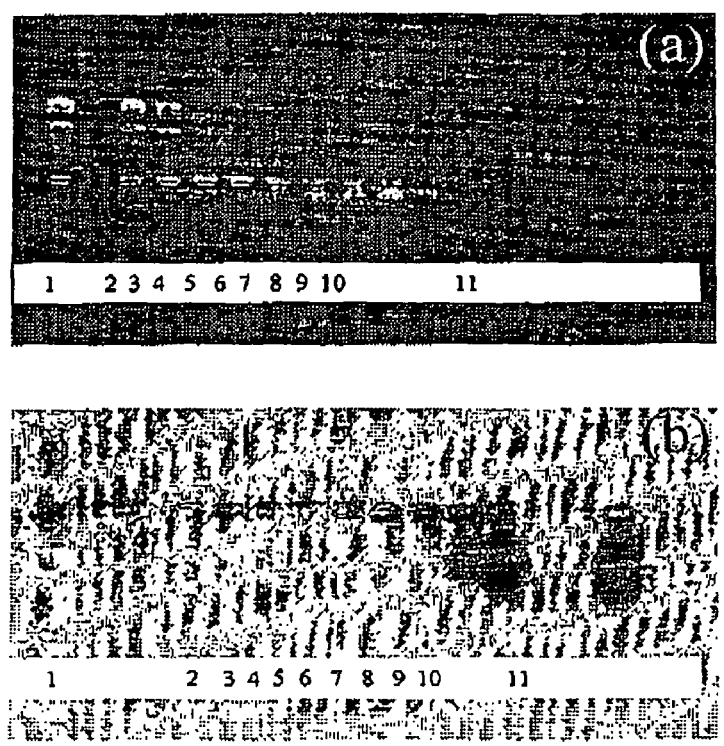
Figure 2

COMPOSITION OF POLYMERS

The present invention relates to compositions comprising polymers and biologically active compounds, especially polymeric drug delivery systems.

DNA delivery has been a flagship in non-viral gene delivery because the promise of therapeutic DNA delivery as a potential cure for many genetic diseases has stimulated much interest over the past decade. With unacceptable immune responses and other adverse events recently reported for viral delivery, nonviral gene delivery becomes even more attractive. However, the main limitation with non-viral delivery is the inefficient transfection, caused mainly by the poor transport of DNA across cell membranes. Various cationic polyelectrolytes have shown promising effects in facilitating gene delivery as these polymers readily conjugate with DNA to neutralize the net negative charges from DNA molecules. However, recent research has indicated that successful polymeric candidates must satisfy a set of requirements. First, although neutralization helps to mediate negative charges in DNA and improve the transport, the polymer must not destabilize the helical structures so that its bioactivity is lost. In addition, it must not impose cytotoxicity to cells either. Cationic polymers such as poly-L-lysine (PLL), polyethylenimine (PEI) and polyamidoamine dendrimer all readily from molecular conjugates with DNA. Unfortunately, high toxicity has been reported from these polymers, which is associated with the dissociation of protons on the primary and secondary amine side chains (the so called proton sponge effect). This event occurs in the endosomal compartment of cell, which activates the complement system leading to cell death. Second, Langer et al have demonstrated that for effective gene delivery, the size of conjugated particles must not be over 150 nm for them to be engulfed by cells Pack, Putnam, Langer, *Biotech. Bioeng.* 2000, 67, 217. Third, the conjugated particles must be readily dispersable in aqueous solution. Unstable aggregates are difficult to administer and are rapidly cleared from systemic administration. These conditions together with the level of the high cost in the synthesis of some of the cationic polymers mean that few existing polymers can meet this set of requirements.

Copolymers of tertiary amine alkyl methacrylates with polyethylene glycol have been investigated for their potential to serve as vectors for gene therapy, by Rungfardthong, U. et al J. Contr. Rel. (2001), 73(2-3), 359-380. Polymers investigated included low polydispersity block copolymers as well as comb polymers formed by statistical copolymerisation of the tertiary amine alkyl methacrylate and a mono-methacrylated oligo(ethyleneglycol) monomer. The incorporation of the PEG moieties enabled colloidally stable complexes of polymer and DNA to be generated. In vitro transfection experiments showed some transfection took place, albeit that lower levels than a control poly-L-lysine system.

In WO-A-99/06055 block copolymers comprising a nonionic block and a cationic block are used to deliver nucleic acids. The non-ionic block may comprise polyacrylamide. The cationic block may comprise polyethylene imine, or a polyimine polymer formed from dibromobutane and N-(3-aminopropyl)-1,3-propane diamine, or a lysine polymer or copolymer (with alanine). Polynucleotide complexed with the copolymers were protected from nuclease attack, and were successful in in vivo and in vitro transfection experiments.

Cationic drugs have been delivered using systems based on anionic polymers, for instance block copolymers comprising non-ionic blocks and anionic blocks. Govender, T. et al in J. Contr. Rel. (2001), 75(3), 249-258 describe non-covalent interactions between a poly(aspartic acid) poly(ethylene glycol) block copolymer with diminazene aceturate, a low molecular weight cationic drug.

Bronich, T. K. et al in Langmuir (2000), 16(2), 481-489, describe block copolymers of polyethylene oxide and poly (sodium methacrylate) with cationic surfactants such as cetylpyridinium bromide. The complexes formed stable dispersions with particle sizes in the range 100 to 200 nm. The authors describe the effect of changing the block length of the PEO block, and of the sodium methacrylate block on the properties of the dispersion.

Similar disclosures are in WO-A-98156348 and WO-A-98/56334, In our earlier patent publications WO-A-98/22516 and WO-A-9822517 we describe polymers, primarily used for coating substrates, having pendant cationic and zwitterionic groups, used in conjunction with anionic biologically active materials such as anionic mucopolysaccharides, especially heparin. Although the polymer is generally coated onto a substrate, and the coated substrate subsequently contacted with the anionic active, it is also suggested that the polymer and active may be premixed in a compatible solvent to form a coating solution.

In our earlier publications WO-A-00/28920 and WO-A-00/29481, we describe polyion complexes formed of oppositely charged polyelectrolytes, at least one of which has pendant zwitterionic groups. The polyion complexes may be used as drug delivery depots, although there are no examples of selection of specific polymers for use with specific actives.

In Langmuir (2000) 16, 5980-5986 Styrkas D. A. et al describe adsorption at a solid-liquid interface of low polydispersity block copolymers formed of a tertiary amino alkyl-methacrylate block and a sulphobetaine-group containing block. The adsorption showed pH-dependent effects which the authors compared to the pH dependent effects of micelle formation of these block copolymers described in earlier work by Bütün, V. et al. in J. Mater. Chem. (1997), 7, 1693.

A new composition according to the invention comprises a block copolymer having an overall ionic charge and associated with the polymer a biologically active compound having a charge opposite that of the polymer and is characterised in that the block copolymer comprises at least one block which has pendant zwitterionic groups and at least one block which comprise ionic groups to confer said overall ionic charge.

The invention is of most value where the biologically active compound is anionic, preferably polyanionic, in nature. The invention is of most value where the active compound is a nucleic acid, for instance an oligonucleotide, having 5 to 50 base residues usually of DNA. For instance the oligonucleotide may be an active anti-sense molecule. The nucleic acid may alternatively be a single strand RNA molecule or a single or double strand DNA molecule. Double stranded DNA may, for instance, comprise genes encoding useful products, especially a plasmid, including control sequences enabling it to be transcribed and translated when transfected into a cell. The invention is thus usefully a gene delivery system. Other anionic actives may be saccharide-containing compounds, proteins or peptides and amphiphilic anionic compounds such as retinoic acid and derivatives.

The invention may also be useful where the biologically active compound is a cationic drug, especially a polycationic drug or an amphiphilic cationic drug. Examples are cetyl and other long chain alkyl-pyridinium compounds, anaesthetics, such as procaine-HCl, rhodamine probes, and low molecular weight drugs such as mexilitine, amiloride HCl, diminazene aceturate and amikicin sulphate.

The composition of the invention is preferably in the form of an aqueous composition or a non-aqueous composition which may be made up to form an aqueous composition by addition of water. In the invention the term "associated with" in relation to the interaction between the polymer and the biologically active compound means that the polymer and the active are electrostatically bound to one another. They are not covalently bound. More preferably the composition comprises polymer and biologically active compound associated with one another in the form of particles having an average diameter of less than 200 nm, preferably less than 150 nm Preferably the particles are in suspension where the composition is the preferred aqueous liquid. Particles of size less than the indicated maximum, are capable of being taken up by cells, so that the biologically active compounds may be delivered intracellularly. Such particles may also be stabilized against settlement in an aqueous composition. Such a composition thus retains useful rheology, enabling it to be handled by usual liquid handling techniques, without having to be thickened or gelled to stabilise the particles against settlement.

The particle size may depend upon the molecular size of the biologically active compound and/or of the copolymer. It will also depend upon other features of the copolymer, for instance the nature of the monomers from which the polymer is formed. Preferably the copolymer has a molecular weight (weight average) less than 500,000, preferably less than 100,000, for instance 50,000 Da.

Generally the zwitterionic block is formed from ethylenically unsaturated monomers including a zwitterionic monomer having the general formula

YBX        I in which

Y is an ethylenically unsaturated group selected from $H_2C=CR-CO-A-$, $H_2C=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

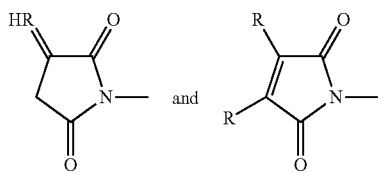

A is —O— or $NR^1$;

$A^1$ is selected from a bond, $(CH_2)_lA^2$ and $(CH_2)_lSO_3$— in which l is 1 to 12;

$A^2$ is selected from a bond, —O—, O—CO—, CO—O, CO—$NR^1$—, —$NR^1$—CO, O—CO—$NR^1$—, $NR^1$—CO—O—;

R is hydrogen or $C_{1-4}$ alkyl;

$R^1$ is hydrogen, $C_{1-4}$ alkyl or BX;

$R^2$ is hydrogen or $C_{1-4}$ alkyl;

B is a bond, or a straight branched alkenediyl, alkylene oxaalkylene, or alkylene (oligooxalkylene) group, optionally containing one or more fluorine substituents;

X is a zwitterionic group.

Preferably X is an ammonium, phosphonium, or sulphonium phosphate or phosphonate ester zwitterionic group, more preferably a group of the general formula II

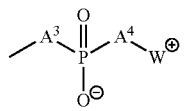

in which the moieties $A^3$ and $A^4$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula

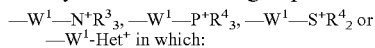

—$W^1$-$Het^+$ in which:

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same of different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus or sulphur-, preferably nitrogen-, containing ring, for example pyridine.

Monomers in which X is of the general formula in which $W^+$ is $W^1N^{\oplus}R^3_3$ may be made as described in our earlier specification WO-A-9301221. Phosphonium and sulphonium analogues are described in WO-A-9520407 and WO-A-9416749.

Generally a group of the formula II has the preferred general formula III

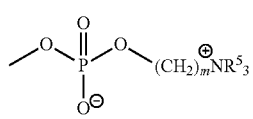

where the groups $R^5$ are the same or different and each is hydrogen or $C_{1-4}$ alkyl, and m is from 1 to 4, in which preferably the groups $R^5$ are the same is preferably methyl.

In phosphobetaine based groups, X may have the general formula IV

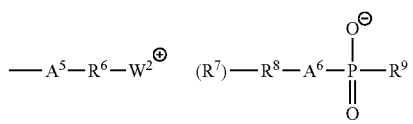

in which $A^5$ is a valence bond, —O—, —S— or —NH—, preferably —O—;

$R^6$ is a valence bond (together with $A^5$) or alkanediyl, —C(O)alkylene- or —C(O)NH alkylene preferably alkanediyl, and preferably containing from 1 to 6 carbon atoms in the alkanediyl chain;

$W^2$ is S, $PR^7$ or $NR^7$;

the or each group $R^7$ is hydrogen or alkyl of 1 to 4 carbon atoms or the two groups $R^7$ together with the heteroatom to which they are attached form a heterocyclic ring of 5 to 7 atoms;

$R^8$ is alkanediyl of 1 to 20, preferably 1 to 10, more preferably 1 to 6 carbon atoms;

$A^6$ is a bond, NH, S or O, preferably O; and $R^9$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula IV may be made by methods as described in JP-B-03-031718, in which an amino substituted monomer is reacted with a phospholane.

In compounds comprising a group of the general formula IV, it is preferred that $A^5$ is a bond;
$R^6$ is a $C_{2-6}$ alkanediyl;
$W^2$ is $NR^7$:
each $R^7$ is $C_{1-4}$ alkyl;
$R^8$ is $C_{2-6}$ alkanediyl;
$A^6$ is O; and
$R^9$ is $C_{1-4}$ alkoxy.

Alternatively X may be a zwitterion in which the anion comprises a sulphate, sulphonate or carboxylate group.

One example of such a group is a sulphobetaine group, of the general formula V

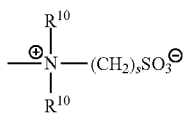

V where the groups $R^{10}$ are the same or different and each is hydrogen or $C_{1-4}$ alkyl and s is from 2 to 4.

Preferably the groups $R^{10}$ are the same. It is also preferable that at least one of the groups $R^{10}$ is methyl, and more preferable that the groups $R^{10}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula VI

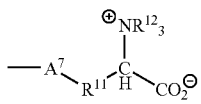

VI in which $A^7$ is a valence bond, O—, —S— or —NH—, preferably —O—, $R^{11}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{12}$ are the same or different and each is hydrogen or alkyl of 1 to 4 carbon atoms, preferably methyl, or two or three of the groups $R^{12}$, together with the nitrogen to which they are attached, form a heterocyclic ring of from 5 to 7 atoms, or the three group $R^{12}$ together with the nitrogen atom to which they are attached form a fused ring heterocyclic structure containing from 5 to 7 atoms in each ring.

Another example of a zwitterion having a carboxylate group is a carboxy betaine —$N^{\ominus}(R^{13})_2(CH_2)_rCOO^{\ominus}$ in which the $R^{13}$ groups are the same or different and each is hydrogen or $R_{1-4}$ alkyl and r is 2 to 6, preferably 2 or 3.

In the zwitterionic monomer of the general formula I it is preferred that the ethylenic unsaturated group Y is $H_2C=CR—CO-A-$. Such acrylic moieties are preferably methacrylic, that is in which R is methyl, or acrylic, in which R is hydrogen. Whilst the compounds may be (meth)acrylamido compounds (in which A is $NR^1$), in which case $R^1$ is preferably hydrogen, or less preferably, methyl, most preferably the compounds are esters, that is in which A is O.

In monomers of the general formula I, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-2'-trimethylammonium ethyl phosphate inner salt (MPC).

The ionic block may be formed of condensation polymers, such as polyethers, polyesters, polyamides, polyanhydrides polyurethanes, polyimines, polypeptides, polyureas, polyacetals, polysaccharides or polysiloxanes. One example of a suitable ionic block is polyethylenimine, copolymers of which with polyalkylene oxides have been investigated as drug delivery components. Preferably, however, the block is formed by radical polymerisation of ethylenically unsaturated monomers.

It is preferred that the ionic block comprise pendant cationic or anionic groups. Cationic pendant groups are, for instance, primary, secondary or tertiary amines, capable of being protonated at pH's in the range 4 to 10. Alternatively a cationic group may be a phosphine. An anionic group may be a phosphate, phosphonate, sulphate, sulphonate, carbonate or preferably carboxylate group.

Suitable ionic monomers from which the ionic block is formed have the general formula VII $Y^1B^1Q$      VII in which $Y^1$ is selected from $H_2C=CR^{14}—CO-A^8-$, $H_2C=CR^{14}—C_5H_4-A^9-$, $H_2C=CR^{14}—CH_2A^{10}$, $R^{10}O—CO—CR^{14}=CR^{14}—CO—O$, $R^{14}CH=CH—CO—O—$, $R^{14}CH=C(COOR^{16})CH_2—CO—O$,

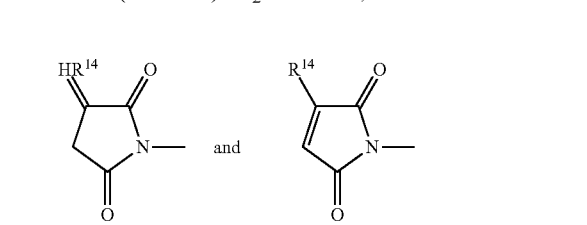

and $A^8$ is —O— or $NR^{15}$;

$A^9$ is selected from a bond, $(CH_2)_qA^{10}$ and $(CH_2)_qSO_3—$ in which q is 1 to 12;

$A^{10}$ is selected from a bond, —O—, —O—CO—, —CO—O, —CO—NR$^{15}$—, —NR$^{15}$CO—, —O—CO—NR$^{15}$—, —NR$^{15}$—CO—O—;

$R^{14}$ is hydrogen or $C_{1-4}$ alkyl;

$R^{15}$ is hydrogen, $C_{1-4}$ alkyl or $B^1Q$;

$R^{16}$ is hydrogen or $C_{1-4}$ alkyl;

$B^1$ is a bond, or a straight branched alkanediyl, alkylene oxaalkylene, or alkylene (oligooxalkylene) group, optionally containing one or more fluorine substituents; and Q is an ionic or ionisable moiety.

By the term ionic monomer, we include ionisable monomers. In the composition where the polymer is associated with the active, the group derived from the ionic monomer should be ionised. Ionisation may take place after polymerisation, however.

Examples of cationic or cationisable groups Q have the formula —NR$^{17}_p$, —PR$^{17}_p$ and SR$^{17}_r$, in which p is 2 or 3, r is 1 or 2, the groups $R^{17}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{17}$ groups may be substituted by amino or hydroxyl groups or halogen atoms.

Preferably Q is NR$^{17}_2$ where $R^{17}$ is $C_{1-12}$-alkyl. Preferably both $R^{17}$'s are the same. Particularly useful results have been achieved where the groups $R^{17}$ are $C_{1-4}$ alkyl, especially ethyl.

Where the monomer of the general formula VII provides anionic or anionisable groups, for instance carboxylate, or carboxylic acid group, $B^1$ is a bond, $A^8$ is —O— and Q is hydrogen. Alternative monomers providing carboxylate or carboxylic acid moieties have $B^1$ as other than a bond, and Q as a carboxylate or carboxylic acid group. Where Q is an anionic or anionisable group other than carboxylate or carboxylic acid group, then $B^1$ is other than a bond, and Q is a group of general formula VIII

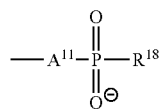

VIII in which $A^{11}$ is a bond, NH, S or O, preferably O; and $R^{18}$ is a hydroxyl, $C_{1-12}$alkyl, $C_{1-12}$-alkoxy, $C_{7-18}$-aralkyl, $C_{7-18}$-arylkoxy, $C_{6-18}$-aryl or $C_{6-18}$-aryloxy group.

Alternatively Q may be a group $SO_3^-$.

Preferably $Y^1$ is $H_2C=CR^{14}COA^8$ where $R^{14}$ is H or $CH_3$ and $A^8$ is O or NH.

$B^1$ is preferably $C_{2-6}$-alkanediyl, preferably $(CH_2)_{2-6}$.

Either or both the zwitterionic and ionic blocks may include comonomers, for instance to provide functionality, control over hydrophobicity, control over pH sensitivity, $pK_A$ or $pK_B$ as the case may be, or as general diluents. For instance comonomers providing functionality may be useful to provide conjugation of pendant groups following polymerisation and/or micelle formation, to targeting moieties, or to provide for conjugation between the biologically active molecule and the polymer. Alternatively, functional groups may allow for crosslinking of the polymer following micelle formation, to confer increased stability on the micellar structure.

Examples of suitable comonomers are compounds of the general formula IX

IX in which $R^{19}$ is selected from hydrogen, halogen, $C_{1-4}$ alkyl and groups COOR$^{23}$ in which $R^{23}$ is hydrogen and $C_{1-4}$ alkyl;

$R^{20}$ is selected from hydrogen, halogen and $C_{1-4}$ alkyl;

$R^{21}$ is selected from hydrogen, halogen, $C_{1-4}$ alkyl and groups COOR$^{23}$ provided that $R^{19}$ and $R^{21}$ are not both COOR$^{23}$, and $R^{22}$ is a $C_{1-10}$ alkyl, a $C_{1-20}$ alkoxycarbonyl, a mono- or di-($C_{1-20}$ alkyl) amino carbonyl, a $C_{6-20}$ aryl (including alkaryl) a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and dialkyl amino and trialkylammonium in which the alkyl groups may be substituted), carboxyl, sulphonyl, phosphoryl, phosphino, (including mono and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups;

or $R^{22}$ and $R^{21}$ or $R^{22}$ and $R^{20}$ may together form —CONR$^{24}$CO in which $R^{24}$ is a $C_{1-20}$ alkyl group.

It is preferred for at least two of the groups $R^{19}$, $R^{20}$, $R^{21}$ and $R^{22}$ to be halogen or, more preferably, hydrogen atoms. Preferably $R^{19}$ and $R^{20}$ are both hydrogen atoms. It is particularly preferred that compound of general formula IX be a styrene-based or acrylic based compound. In styrene based compounds $R^{22}$ represents an aryl group, especially a substituted aryl group in which the substituent is an amino alkyl group, a carboxylate or a sulphonate group. Where the comonomer is an acrylic type compound, $R^{22}$ is an alkoxycarbonyl, an alkyl amino carbonyl, or an aryloxy carbonyl group. Most preferably in such compounds $R^{22}$ is a $C_{1-20}$-alkoxy carbonyl group, optionally having a hydroxy substituent. Acrylic compounds are generally methacrylic in which case $R^{21}$ is methyl.

Preferably the comonomer is a non-ionic comonomer, such as a $C_{1-24}$ alkyl(alk)-acrylate or acrylamide, mono- or di-hydroxy-$C_{1-6}$-alkyl(alk)-acrylate, or -acrylamide, oligo($C_{2-3}$ alkoxy) $C_{2-18}$-alkyl(alk)-acrylate, or -acrylamide, styrene, vinylacetate or N-vinyllactam.

The block copolymer may be a simple A-B block copolymer, or may be an A-B-A or B-A-B block copolymer (where A is the zwitterionic block and B is the ionic block). It may be a star-type polymer with more than two arms of blocks A extending from a core block B or vice versa. It may be a comb type polymer in which the back bone is considered as block A and each tine is a B block or vice versa. It may also be an A-B-C, A-C-B or B-A-C block copolymer, where C is a different type of block C blocks may, for instance, comprise functional, e.g. cross-linking or ionic groups, to allow for reactions of the copolymer, for instance in the novel compositions. Crosslinking reactions especially of A-C-B type copolymers, may confer useful stability on drug-containing micelles. Cross-linking may be covalent, or sometimes, electrostatic in nature. Crosslinking may involve addition of a separate reagent to link functional groups, such as using a difunctional alkylating agent to link two amino groups.

The block copolymers preferably have controlled molecular weights. It is preferable for each of the blocks to have molecular weight controlled within a narrow band, that is to have a narrow polydispersity. The polydispersity of molecular weight should, for instance, be less than 2.0, more preferably less than 1.5, for instance in the range 1.1 to 1.4.

The degree of polymerisation of an ionic block is in the range 5 to 2000, preferably 10 to 500, more preferably 10 to 250. A zwitterionic block has a degree of polymerisation in the range 2 to 1000, preferably 5 to 250 more preferably 10 to 100. Generally the relative lengths of the ionic to zwitterionic blocks is in the range 1:5 to 10:1, preferably 1:1 to 5:1.

It may be possible to synthesise the block copolymer by initial formation of a low polydispersity, low molecular weight initial block using control of initiator and chain transfer agent (which permanently terminates chain formation), with the initial block then being derivatised to act as a suitable radical initiator in a subsequent block forming step, by the technique described by Inoue et al J. Contr. Rel. 1998, 51, 221-229. It may be possible to utilise commercially available relatively low molecular weight low polylispersity ionic polymers as starting materials for a zwitterionic block-forming step, for instance by derivatising the ionic polymer at one or both ends to generate a radical from which polymerisation of monomers including the zwitterionic monomers may be initiated. Preferably, the polymerisation of at least one of the blocks and preferably both the blocks is by controlled radical polymerisation for instance a living radical polymerisation process.

A living radical polymerisation process may be a group transfer radical polymerization, for instance in which an N—O, or other carbon-, sulphur-, and oxygen-centered radical group is transferred from an initiator compound to a monomer. Preferably, however, the process is an atom transfer radical polymerisation process. Preferably such a process is used to form each block of the block copolymer.

In the atom or group transfer radical polymerisation process, the initiator has a radically transferable atom or group, and the catalyst comprises a transition metal compound and a ligand, in which the transition metal compound is capable of participating in a redox cycle with the initiator and dormant polymer chain, and the ligand is either any N—, O—, P— or S—containing compound which can coordinate with the transition metal atom in a σ-bond, or any carbon-containing compound which can coordinate with the transition metal in a π-bond, such that direct bonds between the transition metal and growing polymer radicals and not formed.

Preferably the radical initiator is of the general formula XI $$R^{25}R^{26}R^{27}C—X^2 \qquad XI$$

where:

$X^2$ is selected from the group consisting of Cl, Br, I, $OR^{28}$, $SR^{29}$, $SeR^{29}$, $OP(=O)R^{30}$, $OP(=O)(OR^{30})_2$, $O—N(R^{30})_2$ and $S—C(=S)N(R^{30})_2$, where $R^{28}$ is alkyl of from 1 to 20 carbon atoms in which each of the hydrogen atoms may be independently replaced by halide, $R^{30}$ is aryl or a straight or branched $C_1$-$C_{20}$ alkyl group, and where an $N(R^{30})_2$ group is present, the two $R^{30}$ groups may be joined to form a 5- or 6-membered heterocyclic ring; and $R^{25}$, $R^{26}$ and $R^{27}$ are each independently selected from the group consisting of H, halogen, $C_1$-$C_{20}$ alkyl, $C_3$-$C_8$ cycloalkyl, $C(=O)R^{30}$, $C(=O)NR^{31}R^{32}$, COCl, OH, CN, $C_2$-$C_{20}$ alkenyl, $C_2$-$C_{20}$ alkenyl oxiranyl, glycidyl, aryl, heterocyclyl, aralkyl, aralkenyl, $C_1$-$C_8$ alkyl in which from 1 to all of the hydrogen atoms are replaced with halogen, $C_1$-$C_6$ alkyl substituted with from 1 to 3 substituents selected from the group consisting of $C_1$-$C_4$ alkoxy, aryl, heterocyclyl, $C(=O)R^{30}$, $C(=O)NR^{31}R^{32}$, —$CR^{26}R^{27}X^2$, oxiranyl and glycidyl;

where $R^{30}$ is alkyl of from 1 to 20 carbon atoms, alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups; and $R^{31}$ and $R^{32}$ are independently H or alkyl of from 1 to 20 carbon atoms which alkyl groups, in turn may have substituents selected from acyl, alkoxycarbonyl, alkenoxycarbonyl, aryl and hydroxy, or $R^{31}$ and $R^{32}$ may be joined together to form an alkanediyl group of from 2 to 5 carbon atoms, thus forming a 3 to 6-membered ring;

such that not more than two of $R^{25}$, $R^{26}$ and $R^{27}$ are H.

In the initiator of the general formula V it is preferred that no more than one of $R^{25}$, $R^{26}$ and $R^{27}$, and preferably none, is hydrogen. Suitably at least one, and preferably both of $R^{25}$ and $R^{26}$ is methyl. $R^{27}$ is suitably a group CO—$R^{30}$ in which $R^{30}$ is preferably alkoxy of from 1 to 20 carbon atoms, oligo (alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups.

Since any of $R^{25}$, $R^{26}$ and $R^{27}$ may comprise a substituent $C^{26}R^{27}X^2$, the initiator may be di-, oligo- or poly-functional.

Selection of a suitable initiator is based on various considerations. Where the polymerisation is carried out in the liquid phase, in which the monomers are dissolved, it is preferable for the initiator to be soluble in that liquid phase. The initiator is thus selected for its solubility characteristics according to the solvent system which in turn is selected according to the monomers being polymerised.

Water-soluble initiators include, for instance the reaction product of monomethoxy-capped oligo(ethylene oxide) with 2-bromoisobutyryl bromide (OEGBr), 4-bromo-α-toluic acid or ethyl 2-bromopropanoic acid or 2-(N,N-dimethylamino)ethyl-2'-bromoisobutyrate.

The portion of the initiator —C—$R^{25}R^{26}R^{27}$ becomes joined to the first monomer of the growing polymer chain. The group $X^2$ becomes joined to the terminal unit of the polymer chain. Selection of a suitable initiator is determined in part by whether a terminal group having particular characteristics is required for subsequent functionality. The residue of the initiator at one or other end of the polymer may be reacted with biologically active moieties, such as targetting groups. Alternatively the initiator itself may comprise a group conferring useful targetting or other useful properties without further reaction.

In an atom or group radical transfer polymerisation process the transition metal compound which comprises a component of the catalyst is 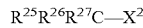, where:

$M_t^{n+}$ may be selected from the group consisting of $Cu^{1+}$, $Cu^{2+}$, $Fe^{2+}$, $Fe^{3+}$, $Ru^{2+}$, $Ru^{3+}$, $Cr^{2+}$, $Cr^{3+}$, $Mo^{2+}$, $Mo^{3+}$, $W^{2+}$, $W_{3+}$, $Mn^{2+}$, $Mn^{3+}$, $Mn^{4+}$, $Rh^{3+}$, $Rh^{4+}$, $Re^{2+}$, $Re^{3+}$, $Co^+$, $Co^{2+}$, $Co^{3+}$, $V^{2+}$, $V^{3+}$, $Zn^+$, $Zn^{2+}$, $Ni^{2+}$, $Ni^{3+}$, $Au^+$, $Au^{2+}$, $Ag^+$ and $Ag^{2+}$;

$X^3$ is selected from the group consisting of halogen, $C_1$-$C_6$-alkoxy, $(SO_4)_{1/2}$, $(PO_4)_{1/3}$, $(R^{33}PO_4)_{1/2}$, $(R^{33}_2PO_4)$, triflate, hexafluorophosphate, methanesulphonate, arylsulphonate, CN and $R^{34}CO_2$, where $R^{33}$ is aryl or a straight or branched $C_{1-20}$ alkyl and $R^{34}$ is H or a straight or branched $C_1$-$C_6$ alkyl group which may be substituted from 1 to 5 times with a halogen; and n is the formal charge on the metal ($0 \leq n \leq 7$).

Preferably $X^3$ is halide, most preferably chloride or bromide. Particularly suitable transition metal compounds are based on copper or ruthenium, for instance CuCl, CuBr or $RuCl_2$.

In the catalyst, the ligand is preferably selected from the group consisting of:

a) compounds of the formulas:

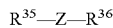

and

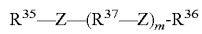

where:

$R^{35}$ and $R^{36}$ are independently selected from the group consisting of H, $C_1$-$C_{20}$ alkyl, aryl, heterocyclyl and $C_1$-$C_6$ alkoxy, $C_1$-$C_4$ dialkylamino, $C(=O)R^{38}$, and $A^{11}C(=O)R^{40}$, where $A^{11}$ may be $NR^{41}$ or O; $R^{38}$ is alkyl of from 1 to 20 carbon atoms, aryloxy or heterocyclyloxy; $R^{40}$ is H, straight or branched $C_1$-$C_{20}$ alkyl or aryl and $R^{41}$ is hydrogen, straight or branched; $C_{1-20}$-alkyl or aryl; or $R^{35}$ and $R^{36}$ may be joined to form, together with Z, a saturated or unsaturated ring;

Z is O, S, $NR^{42}$ or $PR^{42}$, where $R^{42}$ is selected from the same group as $R^{35}$ and $R^{36}$, and where Z is $PR^{42}$, $R^{42}$ can also $C_1$-$C_{20}$ alkoxy or Z may be a bond, $CH_2$ or a fused ring, where one or both of $R^{35}$ and $R^{36}$ is heterocyclyl, each $R^{37}$ is independently a divalent group selected from the group consisting of $C_1$-$C_8$ cycloalkanediyl, $C_1$-$C_8$ cycloalkenediyl, arenediyl and heterocyclylene where the covalent bonds to each Z are at vicinal positions or $R^{37}$ may be joined to one or both of $R^{35}$ and $R^{36}$ to formulate a heterocyclic ring system; and m is from 1 to 6;

b) CO;

c) porphyrins and porphycenes, which may be substituted with from 1 to 6 halogen atoms, $C_{1-6}$ alkyl groups, $C_{1-6}$ alkoxy groups, $C_{1-6}$ alkoxycarbonyl, aryl groups, heterocyclyl groups, and $C_{1-6}$ alkyl groups further substituted with from 1 to 3 halogens;

d) compounds of the formula $R^{43}R^{44}C(C(=O)R^{45})_2$, where $R^{45}$ is $C_{1-20}$ alkyl, $C_{1-20}$ alkoxy, aryloxy or heterocyclyloxy; and each of $R^{43}$ and $R^{44}$ is independently selected from the group consisting of H, halogen, $C_{1-20}$ alkyl, aryl and heterocyclyl, and $R^{43}$ and $R^{44}$ may be joined to form a $C_{1-8}$ cycloalkyl ring or a hydrogenated aromatic or heterocyclic ring, of which the ring atoms may be further substituted with 1 to 5 $C_{1-6}$ alkyl groups, $C_{1-6}$ alkoxy groups, halogen atoms, aryl groups, or combinations thereof; and e) arenes and cyclopentadienyl ligands, where said cyclopentadienyl ligand may be substituted with from one to five methyl groups, or may be linked through and ethylene or propylene chain to a second cyclopentadienyl ligand.

Selection of a suitable ligand is, for instance, based upon the solubility characteristics and/or the separability of the catalyst from the product polymer mixture. Generally it is desired for the catalyst to be soluble in a liquid reaction mixture, although under some circumstances it may be possible to immobilise the catalyst, for instance an a porous substrate. For the preferred process, which is carried out in the liquid phase, the ligand is soluble in a liquid phase. The ligand is generally a nitrogen containing ligand. The preferred ligand may be a compound including a pyridyl group, such as bipyridine, a compound including a pyridyl group and an imino moiety such as:

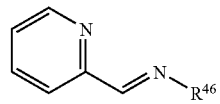

where $R^{46}$ is a suitable alkyl group, the substituent being variable and adaptable to confer desired solubility characteristics, triphenylphosphine or 1,1,4,7,10,10-hexamethyl-triethylene tetramine.

Such ligands are usefully used in combination with copper chloride, copper bromide and ruthenium chloride transition metal compounds as part of the catalyst.

A living radical polymerisation process is preferably carried out to achieve a degree of polymerisation in the or each block in the range 5 to 500. Preferably the degree of polymerisation is in the range 10 to 100, more preferably in the range 10 to 50. In the preferred group or atom transfer radical polymerisation technique, the degree of polymerisation is directly related to the initial ratios of initiator to monomer. Preferably the ratio is in the range 1:(5 to 500), more preferably in the range of 1:(10 to 100), most preferably in the range 1:(10 to 50).

The ratio of metal compound and ligand in the catalyst should be approximately stoichiometric, based on the ratios of the components when the metal ion is fully complexed. The ratio should preferably be in the range 1:(0.5 to 2) more preferably in the range 1:(0.8:1.25). Preferably the range is about 1:1.

In the living radical polymerisation process, the catalyst may be used in amounts such that a molar equivalent quantity as compared to the level of initiator is present. However, since catalyst is not consumed in the reaction, it is generally not essential to include levels of catalyst as high as of initiator. The ratio of catalyst (based on transition metal compound) to initiator is preferably in the range 1:(1 to 50), more preferably in the range 1:(1 to 10).

Whilst the polymerisation reaction may be carried out in the gaseous phase, it is more preferably carried out in the liquid phase. The reaction may be heterogeneous, that is comprising a solid and a liquid phase, but is more preferably homogeneous. Preferably the polymerisation is carried out in a single liquid phase. Where the monomer is liquid, it is sometimes unnecessary to include a non-polymerisable solvent. More often, however, the polymerisation takes place in the presence of a non-polymerisable solvent. The solvent should be selected having regard to the nature of the zwitterionic monomer and any comonomer, for instance for its suitability for providing a common solution containing both monomers. The solvent may comprise a single compound or a mixture of compounds.

It has been found that, especially where the zwitterionic monomer is MPC, that it is desirable to include water in the polymerisation mixture. Preferably water should be present in an amount in the range 10 to 100% by weight based on the weight of ethylenically unsaturated monomer. Preferably the total non-polymerisable solvent comprised 1 to 500% by weight based on the weight of ethylenically unsaturated monomer. It has been found that the zwitterionic monomer and water should be in contact with each other for as short a period as possible prior to contact with the initiator and catalyst. It may be desirable therefore for all the components of the polymerisation other than the zwitterionic monomer to be premixed and for the zwitterionic monomer to be added to the premix as the last additive.

It is often desired to copolymerise MPC or other zwitterionic monomer with a comonomer which is insoluble in water. In such circumstances, a solvent or cosolvent (in conjunction with water) is included to confer solubility on both MPC and the more hydrophobic monomer. Suitable organic solvents are ethers, esters and, most preferably, alcohols. Especially where a mixture of organic solvent and water is to used, suitable alcohols are $C_{1-4}$-alkanols. Methanol is found to be particularly suitable in the polymerisation process of the invention.

The process may be carried out at raised temperature, for instance up to 60 to 80° C. However it has been found that the process proceeds sufficiently fast at ambient temperature.

The living radical polymerisation process has been found to provide blocks of zwitterionic monomers having a polydispersity (of molecular weight) of less than 1.5, as judged by gel permeation chromatography. Polydispersities in the range 1.2 to 1.4 for the or each block are preferred.

In the composition the relative amounts of biologically active compound and of polymer may be about stoichiometric in terms of the counterionic groups. Alternatively there may be an excess of one charge over the other for instance up to 5 or 10 times excess. The level may depend on stability factors or on interactions of the components of the composition with biological systems. For instance, Rungsardthong, et al, op. cit., show that the level of excess cationic polymer over DNA may affect transfection levels. Appropriate levels of the biologically active compound and polymer may be determined by experimentation. The particles may be analysed for their ζ potential. This technique determines the presence of overall charge on the surface of particles. Stability and activity may be determined by available assays. It has been found that the presence of zwitterionic groups in the aqueous composition stabilises the dispersed particles, without requiring addition of stabilisers, or using an excess of drug or polymer. The compositions may additionally contain buffers or other salts or pH-modifying components, stabilisers etc.

Further probes into the particles in the composition may be by dynamic light scattering investigations, which may give a value for average aggregate diameters. Small angle neutron scattering may also be used to provide structural details inside the particles, as may electron microscopy, for instance transmission electron microscopy (TEM).

According to a further aspect of the invention there is provided a process for forming the novel composition in which an aqueous dispersion of a block copolymer having an overall ionic charge and comprising at least one block which has pendant zwitterionic groups and at least one block which comprise ionic groups to confer said overall ionic charge, is contacted with a biologically active compound having a charge opposite that of the block copolymer, to form an aqueous suspension of block copolymer and associated active.

In the process the dispersion of copolymer may be a solution including a colloidal solution or a suspension. The copolymer may be in the form of micelles, for instance. The pH is selected so as to ensure that the counterionically charged groups in polymer and ionic groups in biologically active attract each other electrostatically.

Preferably the active is pre-dissolved in water before being contacted with the copolymer dispersion, although direct dissolution into the block copolymer dispersion may be possible. We have found that simple physical mixing of the aqueous solutions results in suspended particles of a suitable size for administration for therapeutic purposes.

It is believed that the compositions will be particularly useful for allowing gene or ODN delivery into cells. Thus the compositions may be useful for administering to the patients in need of therapy by the biologically active molecule. The compositions may thus be suitable for administration IV, IP or IM for instance. The effect of the compositions on intracellular delivery may be illustrated using in vitro test systems. For instance delivery of genes into cells may be determined by using, as the biologically active molecule, a plasmid encoding a model gene, the product of which may be observed. Suitable vectors are available encoding luciferase and/or β-galactosidase. Such tests may be carried out in conjunction with cell proliferation assays using tritium-labelled thymidine and using as positive controls known cationic polymer delivery systems such as poly-L-lysine, or PEO-PEI block copolymers.

Cytotoxicity determinations may be conducted. Such tests may, for instance, be useful to determine the base toxicity of the polymers themselves. Alternatively, where the drug to be delivered is intended to be cytotoxic, a cytotoxicity test may reveal the success of the drug delivery system. Stability of the compositions may be investigated, for instance by contacting the compositions with pH modifiers, salts and/or serum and determining physical and biologically stability. Resistance to degradation by enzymic reactions, such as attack of nucleic acid by nucleases is relevant to the utility of the invention in formulating nucleic acids, as is the effect on ethidium bromide intercalation.

The following examples illustrate the invention.

EXAMPLE 1

A-B block copolymers were formed by an atom transfer polymerisation with MPC being homopolymerised in a first block forming step using an oligo(ethylene glycol) initiator as described by Ashford E. J. et al in Chem. Commun. 1999, 1285 (the reaction product of monomethoxy-capped oligo (ethylene glycol) and 2-bromoisobutyryl bromide) in the presence of bipyridine ligand and copper (I) bromide catalyst. DEA (diethylaminoethyl methacrylate) was polymerised in a second block forming step. The degree of polymerisation for each block is indicated in Table 1 showing the results.

The reaction conditions were [MPC]=2.02M (6.0 g in 10 ml methanol), [MPC]:[OEG-Br]:[CuBr]:[bipy]=(30 or 20 as shown in Table 1):1:1:2, T=20° C.; MPC was polymerised first in all cases followed by addition and polymerisation of an appropriate amount of neat DEA. Almost complete monomer conversion was achieved after the time indicated in Table 1 for the diblock, as indicated by $^1$H NMR spectroscopy (no residual vinyl double bonds). The reaction mixture was diluted with methanol and passed through a silica column to remove residual ATRP catalyst. After solvent evaporation, the products were dried under vacuum at room temperature.

TABLE 1

Data of the polymerization of MPC - DEAEMA diblock copolymers in methanol

| Ex # | Comonomer | MPC In copolymer (mol %) | TargetDp | [Amine] (M) | Time for >99% Conversion MPC HOMO (mins) | Time for >99% Conversion MPC Diblock (h) | Mn (AGPC) MPC(a) HOMO | Mn (AGPC) MPC(b) Diblock | Mw/Mn MPC HOMO | Mw/Mn MPC Diblock |
|---|---|---|---|---|---|---|---|---|---|---|
| 1 | DEA | 50 | 20:20 | 1.35 | 180 | 20 | 6200 | 14000 | 1.15 | 1.22 |
| 2 | DEA | 33 | 10:20 | 1.35 | 180 | 21 | 3500 | 11000 | 1.17 | 1.29 |
| 3 | DEA | 50 | 30:30 | 2.02 | 130 | 20 | 10000 | 21000 | 1.18 | 1.30 |
| 4 | DEA | 33 | 30:60 | 4.04 | 130 | 22 | 11000 | 31000 | 1.19 | 1.29 |
| 5 | DEA | 23 | 30:100 | 6.73 | 130 | 23 | 11000 | 43000 | 1.19 | 1.28 |

DEA = diethylaminoethylmethacrylate
AGPC = aqueous gel permeation chromatography The MPC-DEA block copolymers were dissolved in McIlvaines buffer at a concentration of 1 mM and at pH 4. The pH was then adjusted upwards with NaOH to pH 8, and 10.8, so the micelles would form. A series of half dilutions were then prepared from the micellised polymers, using McIlvaines buffer of the same pH as the polymer solution.

To demonstrate the polymer shift from unimer to micelle state in response to pH increase, a control of polymer at pH 4 was carried using the same technique and conditions as that used for the pH8 and pH10.8 samples using the 30:60 MPC:DEA block copolymer. The polymer solutions at pH4 and pH8 were also analysed using photon correlation spectroscopy (PCS) to measure the hydrodynamic diameter of the particles based on the intensity of scattered light, and calculated using the Stokes-Einstein equation, as described in ISO13321 British Standards Institution. 1997, BS3046: Part 8: 1997: ISO 13321: "Photon correlation spectroscopy", in Methods for determination of is particle size distribution, BSI publications, Chiswick, UK, p 1-21, with subsequent analysis and determination of intensity size distributions using the CONTIN algorithm. Measurement was carried out using a Malvern Zetasizer 3000HS, using a 10 mW He—Ne laser, with a wavelength of 633 nm, and a high sensitivity avalanche photodiode detector fixed at a 90 degree angle to the laser, at a temperature of 25° C. Samples were sonicated for 5 minutes and filtered through a 0.2 micron filter prior to measurement, to remove any aggregation and possible dust contamination.

In FIG. 1 the shift from unimer to micelle in response to increased pH can be seen. At pH4 (grey shaded curve) only unimers with a mean diameter of 11.3 nm are present, however when the pH is raised to pH8 (black shaded curve) there is a clear increase in mean diameter from 11.3 nm up to 37.5 nm, indicating the unimers have undergone micellar self assembly in response to increased pH.

EXAMPLE 2

Generic Block Copolymer Preparation by Sequential Monomer Addition

MPC was polymerized first in 10 ml methanol, using [MPC]:[OEGBr]:[CuBr]:[bpy]=X:1:1:2 (where X is the number of moles of MPC used to achieve the desired target degree of polymerization) under a nitrogen atmosphere at 20° C. After 2.0 h, the MPC conversion was greater than 99%, and the MPC homopolymer obtained had a low polydispersity (Mw/Mn=1.09 with Mn=10,000 vs. poly(ethylene oxide) standards. Then the appropriate amount of the comonomer 2-dimethylaminoethyl methacrylate (DMA) was added to this reaction solution, to give a particular target degree of polymerization for the second block. After 40 h, $^1$H NMR studies indicated that both monomers had been consumed. The reaction solution was passed through a silica gel column to remove the spent ATRP catalyst, which resulted in the loss of around 10% copolymer due to adsorption onto the silica. After solvent evaporation, the solid copolymer was washed with an excess of a suitable solvent to remove any traces of residual comonomer, redissolved in water and then freeze-dried overnight. The molecular weight and polydispersity of the resulting polymers was determined by aqueous GPC using poly(2-vinylpyridine) standards. Table 2 summarises data for a series of MPC-DMA diblock copolymers.

TABLE 2

| | Target Composition | Time for >95% Conversion[a] Homo (h) | Time for >95% Conversion[a] Diblock (h) | Mn (GPC)[b] Homo | Mn (GPC)[b] Diblock | Mw/Mn[b] Homo | Mw/Mn[b] Diblock | Cu[c]/ ppm |
|---|---|---|---|---|---|---|---|---|
| 1 | $MPC_{30}$-$DMA_{100}$ | 2.0 | 48 | 10,000 | 46,000 | 1.17 | 1.32 | 1.7 |
| 2 | $MPC_{30}$-$DMA_{60}$ | 2.0 | 24 | 10,000 | 34,000 | 1.15 | 1.28 | 1.5 |
| 3 | $MPC_{30}$-$DMA_{40}$ | 2.0 | 20 | 9,000 | 25,000 | 1.15 | 1.26 | 1.2 |
| 4 | $MPC_{30}$-$DMA_{30}$ | 2.0 | 15 | 10,000 | 22,000 | 1.19 | 1.27 | 2.0 |
| 5 | $MPC_{30}$-$DMA_{20}$ | 2.0 | 10 | 10,000 | 18,000 | 1.18 | 1.22 | 0.8 |
| 6 | $MPC_{30}$-$DMA_{10}$ | 2.0 | 8 | 10,000 | 15,000 | 1.17 | 1.21 | 0.6 |
| 7 | $MPC_{60}$-$DMA_{40}$ | 1.6 | 24 | 14,000 | 22,000 | 1.18 | 1.28 | 0.5 |

TABLE 2-continued

| Target Composition | Time for >95% Conversion[a] | | Mn (GPC)[b] | | Mw/Mn[b] | | Cu[c]/ |
| --- | --- | --- | --- | --- | --- | --- | --- |
| | Homo (h) | Diblock (h) | Homo | Diblock | Homo | Diblock | ppm |
| 8 MPC$_{40}$-DMA$_{40}$ | 1.3 | 24 | 11,000 | 19,000 | 1.15 | 1.27 | 0.9 |
| 9 MPC$_{20}$-DMA$_{40}$ | 1.1 | 20 | 6,000 | 15,000 | 1.10 | 1.25 | 0.4 |
| 10 MPC$_{10}$-DMA$_{40}$ | 1.0 | 18 | 3,000 | 30,000 | 1.07 | 1.23 | 0.4 |

[a]As determined by $^1$H NMR spectroscopy.
[b]As determined by aqueous GPC at pH 2 (0.5M acetic acid + 0.03M sodium acetate) using poly(2-vinylpyridine) calibration standards.
[c]As determined by inductively-coupled plasma atomic emission spectroscopy [ICP-AES].

EXAMPLE 3

Agarose Gel Electrophoresis

The interaction between plasmid DNA (Calf thymus DNA, Sigma UK) and polymers was investigated by electrophoresis on agarose gel (Promega Corporation, Madison, USA). Complexes were prepared corresponding to monomer:nucleotide molar ratio (mole/mole) in terms of DMA polymer repeating units: DNA nucleotides. Complexes at monomer:nucleotide molar ratio of 0.2:1, 0.5:1, 1:1, 1.2:1, 1.4;1, 1.8:1, 2:1, 5:1 and 10:1 were placed in the wells of the 0.6% agarose gel containing ethidium bromide (0.6 μg/ml). Solution containing 1 mg plasmid DNA was used. Controls for free DNA and free polymers were also applied on the gel. Gel running buffer was 40 mM Tris acetate (pH 7.4) and 1 mM EDTA. The gel was run at 70 V for one hour, after which the DNA was visualized on a UV transilluminator. Polymer was visualized by staining the gel with dye (Coomassie blue in 10% acetic acid and 10% ethanol) and subsequent washing with the destaining solution (same as the staining solution without the dye).

Electrophoretic movement of the DNA molecule within the gel is inhibited by complexation with the MPC polycation, in this case MPC20-DMA20. Lanes 1 and 11 represent the controls of free plasmid DNA and free polymer respectively. Lanes 2-10 represent the polycation monomer to DNA base ratios of 0.2, 0.5, 1, 1.2, 1.4, 1.8, 2, 5 and 10. Retardation of complexed/condensed DNA in the application well can be seen in the Figures. Visualisation of the gel in FIG. 2(a) was achieved by DNA intercalating fluoresce probe (ethydium bromide) incorporation in the gel. The presence of migrating DNA in lanes 2-6 indicate that there is insufficient polymer present to completely condense all of the DNA that is present into an aggregate. Eventual inhibition of the DNA migrating band in FIG. 2(a) occurred in lane 7, which was equivalent to ratio 1.4. The free polymer bands in FIG. 2(b) indicated the presence of excess of the polymer at certain ratios which is not associated with the condensates. Likewise, appearance of free polymer bands appear at Lane 7 and greater, again at a ratio of 1.4. Thus, the MPC-DMA diblock polymer system is capable of condensing with DNA, and for the MPC20-DMA20 system studied here, a ratio of 1:1.4 for DNA:polymer was required to produce an optimum aggregate.

EXAMPLE 4

DNA Binding Affinity by Ethidium Bromide Displacement

An assessment of the MPC-polycations' ability to form complexes with DNA was made by measuring changes in the fluorescence of ethidium bromide-DNA complexes. Loss of ethidium bromide fluorescence is thought to result from polyelectrolyte binding leading to a DNA complexation, resulting in expulsion of intercalated ethidium bromide molecules. The level of fluorescence reduction is related to the affinity of MPC polycation-DNA binding. Ethidium bromide (2 μg, 1 mg/ml) was added to 10 fold diluted phosphate buffer saline (1000 μl) in cuvettes and mixed by gentle agitation Fluorescence was recorded in triplicate at $I_{ex}$ 560 and $I_{em}$ 605 nm in a Hitachi F-4500 fluorescence spectrophotometer. Calf thymus DNA (10 μg) was added and fluorescence measured again. An aliquot of polymer was then titrated into the solution to a calculated monomer nucleotide molar ratio. Samples were mixed gently and readings were taken after 1-2 min. Duplicate samples were used for each measurement Complex formation in the presence of salt was assessed by varying NaCl concentration i.e. 10, 25, 50, 1000, 2000 mM in a ten fold dilution of phosphate buffer saline (1000 μl). Control readings were taken using PEG 4000 Da solution.

The relative fluorescence was calculated as below:

$$\% \text{Relative } Fluor'ce = \frac{Fluor'ce(obs) - Fluor'ce(\text{EtBr})}{Fluor'ce(\text{DNA} + \text{EtBr}) - Fluor'ce(\text{EtBr})} \times 100$$

Fluor'ce (obs)=Fluor'ce of DNA+Ethidium Bromide+polymer
Fluor'ce (EtBr)=Fluor'ce of Ethidium Bromide alone
Fluor'ce (DNA+EtBr) Fluor'ce of DNA+Ethidium Bromide FIG. 3 compares the ethidium bromide displacement of a number of polymers, including
  (i) the MPC30-DMA30 diblock made in example 2,
  (ii) DMA homopolymer, having an average MW 6050 and polyolispersity 1.8 "DMAEMA".
  (iii) polyvinylpyrrolidone (Aldrich) with average MW29KD (PVP).
  (iv) DMA-PEG linear diblock copolymer having an average MW9750, a DMA content of 40 mol % and polydispersity 1.25 (synthesised by an oxyanionic polymerisation as described in Varnvakaki, M et al in Macromolecules 32 (1999) 2088-2090). It is similar to one of the polymers tested in Rungsardthong et al., op cit.
  (v) two diblock copolymers formed by polymerising a first block of DMA and a second block of methoxy-capped oligo (ethylene glycol) methacrylate having an average number of ethylene glycol repeat units of 7.5 as described in more detail by Bailey, L, PLD thesis, University of Sussex 2000. The polymers were similar to those tested by Rungsardthong et al., op cit. DMA-OEGMA15 has an average MW of 11990, a polydispersity of 1.09 and a DMA content of 66 mol %. DMA-OEGMA7 has an average MW of 9630, a polydispersity of 1.12 and a DMA content of 84 mol %.

A reduction in the relative fluorescence indicates ability of the polymer to interact with DNA displacing the probe. Clearly, the MPC diblock and DMA homopolymer have the ability to condense the DNA, as a reduction in the relative fluorescence indicates ability of the polymer to interact with the DNA and thus displacing the probe. The control PVP polymer did not have this capability. The DMA-MPC diblock required a higher ratio of cationic monomer polymer to DNA in order to condense compared to DMA monopolymer or any of the poly(ethylene-glycol)-group containing polymers. This may be a consequence of the MPC block of the polymer affecting the condensation process.

Figure 4:
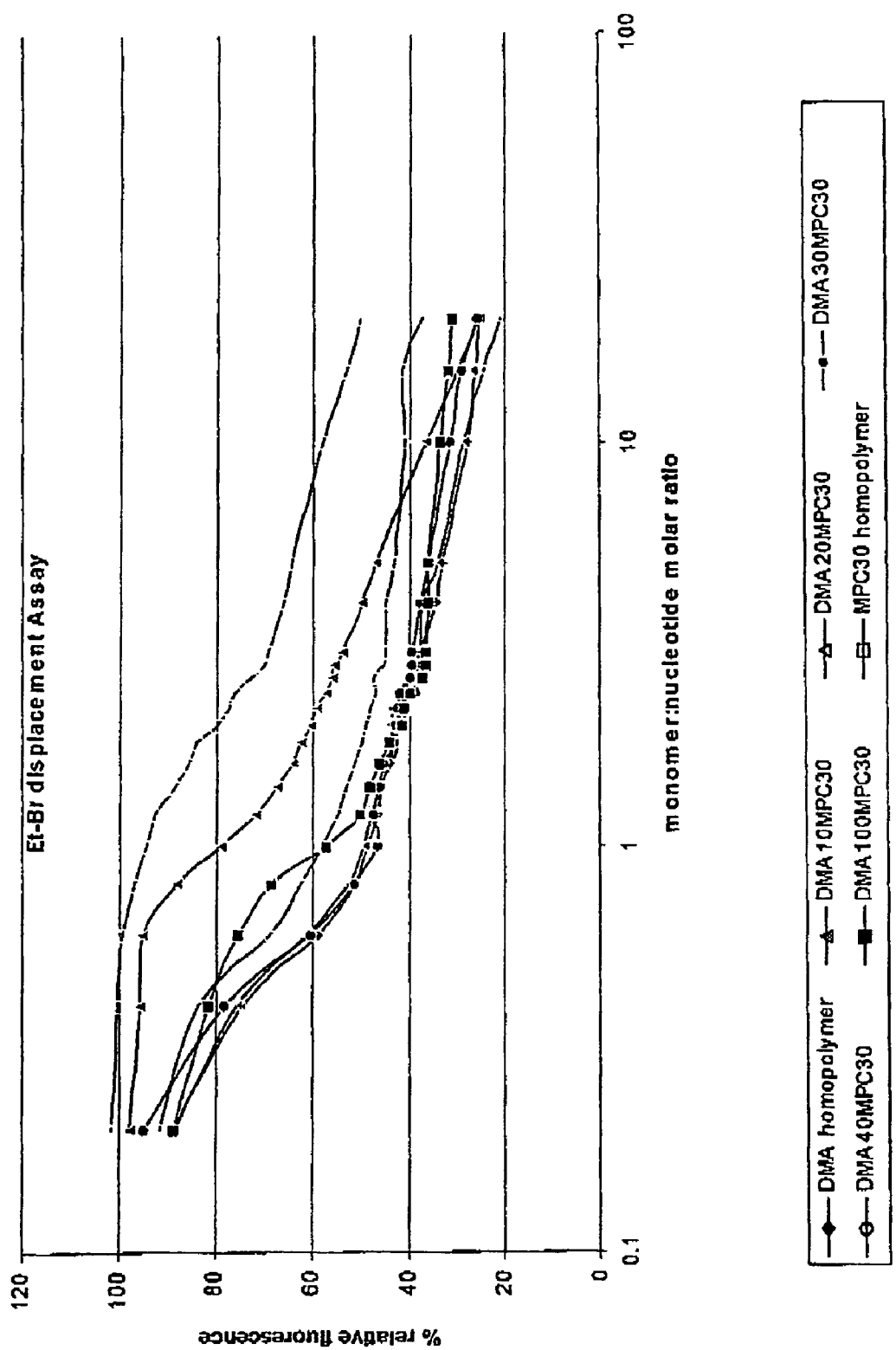
Figure 5:
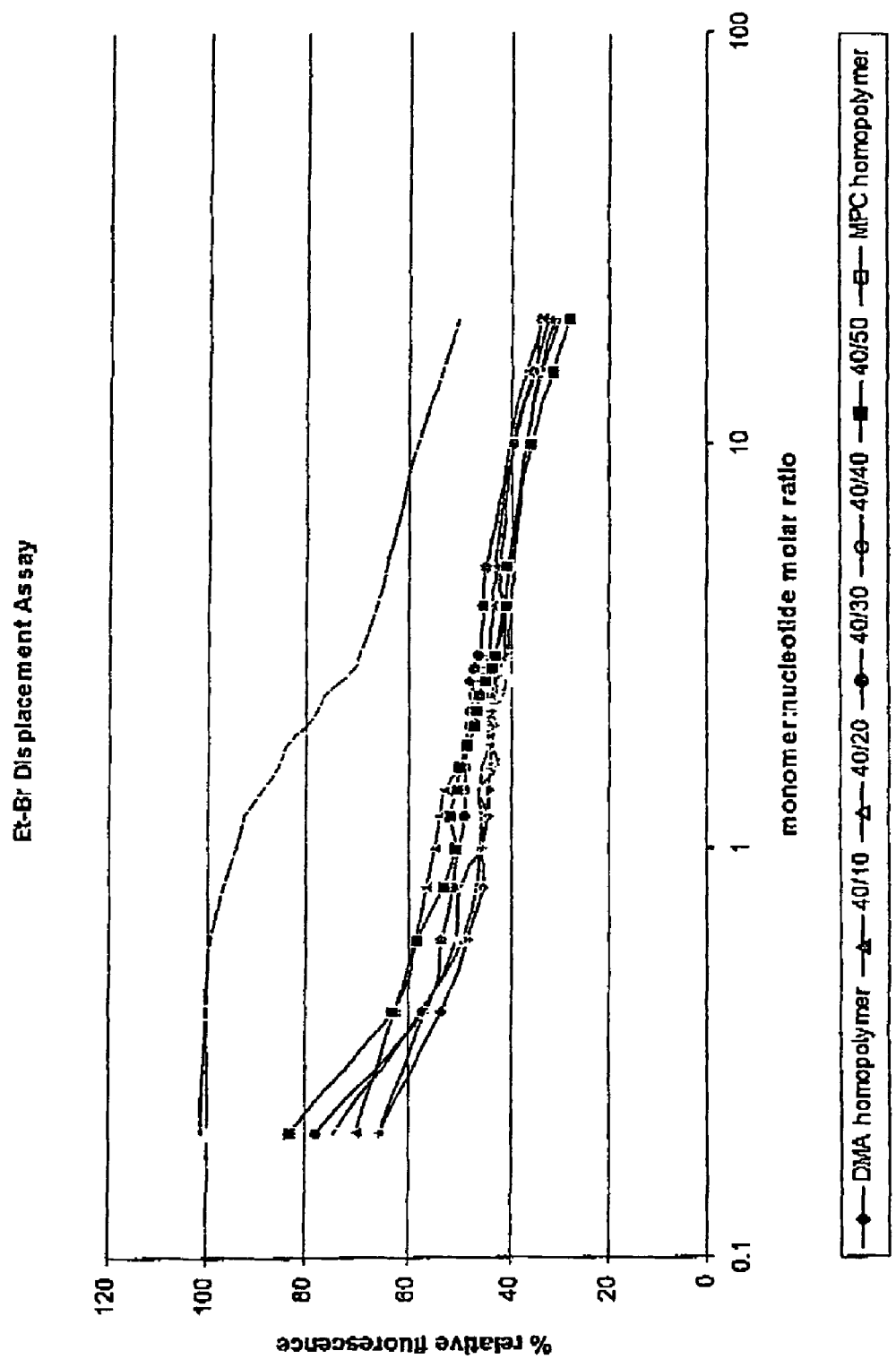

FIG. 4 shows the ethidium bromide displacement ability for a series of DMAx-MPC30 copolymers (where x=10, 20, 30, 40, 100) at different monomer nucleotide ratios. There was a rapid decrease in the relative fluorescence while increasing the ratio from 0.2 to 1.0. Between ratios 1.0 to 5.0, a gradual decrease in fluorescence was observed with increasing ratio. At ratios higher than 5.0, a plateau was reached. The minimal level of fluorescence reached ranged from 25-40%. The $DMA_{10} MPC_{30}$ copolymer showed the least decrease in fluorescence initially, indicating that it was least able to bind with DNA. The $DMA_{40}MPC_{30}$ showed a lesser extent of DNA binding when compared with other polymers. For all other DMA-co-MPC polymers, the displacement profile was similar to the DMA homopolymer. Thus, the presence of the hydrophilic MPC does not appear to hinder the interaction between DNA and DMA portion of the copolymers. Indeed, the MPC homopolymer showed some ability to interact with the DNA, but to a much lesser extent than the copolymers. FIG. 5 shows the effect of varying the MPC block length for DMA40MPCX block copolymers; this had little impact on the ability to interact with the DNA for MPC block lengths 10 to 50 monomer units long (i.e X=10-50).

EXAMPLE 5

Scattering Intensity and Particle Size Characterisation

The scattering intensity of polymer/DNA complexes was measured by a Malvern S4700 PCS system (Malvern Instrument, Malvern UK). The study was undertaken by the titration of polymers into 10 μg of calf thymus DNA prepared in ten fold diluted phosphate buffer saline (500 μl). The samples were then mixed by gentle agitation after the aliquot of polymer was added. Measurements were made at different monomer:nucleotide molar ratios at 25° C. using a 40.7 mW laser and a scattering angle of 90°. The scattering intensity of each sample was obtained as the mean of 10 determinations. Data presented are the mean of a minimum of 2 replicate titrations.

The diameter of polymer/DNA complexes was also measured by a Malvern S4700 PCS system. Individually prepared complexes of pCT0129L DNA (10 μg) (pCT0129LDNA, a 4.3-kb expression vector containing the chloramphenicol actyltransferase reporter gene was used as obtained from Gene Medicine Inc (Texas, USA)) in ten fold diluted phosphate buffer saline (500 μl) and addition of a aliquot polymer were measured at different monomer nucleotide molar ratios. The measurements were performed at 25° C., 40.7 mW laser and a scattering angle 90°. The particle size of each sample was obtained by using CONTIN analysis as the mean hydrodynamic diameter±standard deviation of six determinations including scattering intensity and polydispersity.

Figure 6:
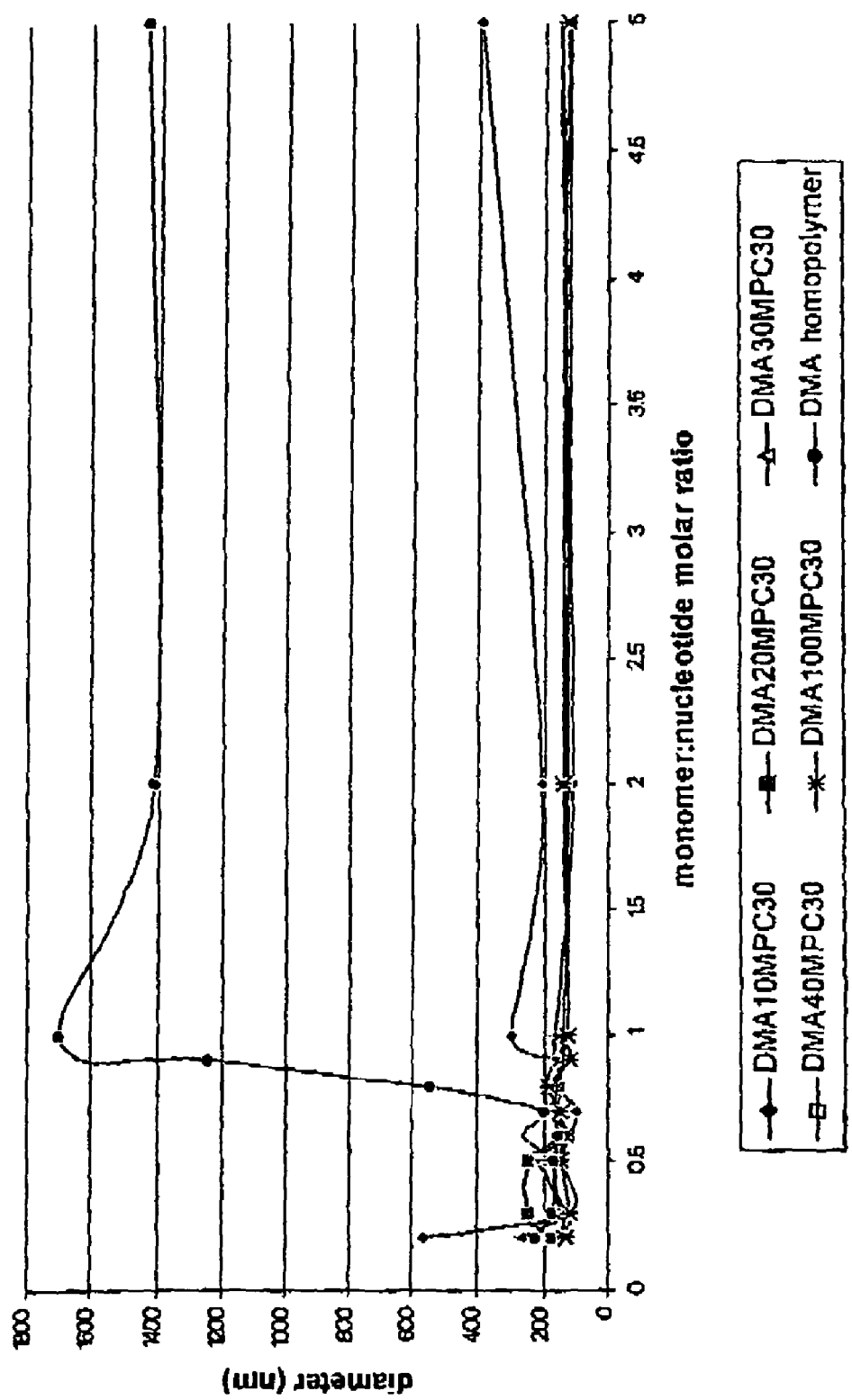

Using PCS to monitor complexation, as the monomer: nucleotide molar ratios exceeded 1.0, the size of complexes formed by the DMA homopolymer increased significantly to above 1 μm, indicating that agglomeration of particles occurred (FIG. 6). At ratio 1.0, the complexes become neutral and there is insufficient electrostatic repulsion to stabilise the complexes and prevent aggregation.

Table 3 shows the particles size and scattering intensity for MPC30 DMAX diblock copolymers. Table 4 show the particle size and scattering intensity data for MPCX-DMA 40 diblocks.

The DMA MPC polymers complexes exhibited a different behaviour. Generally, the complexes formed by MPC-based copolymers were colloidally stable, with an average size of 150 nm. The complexes remained small and discrete as the monomer nucleotide molar ratios exceeded 1.0. Incorporation of hydrophilic MPC moiety to cationic polymer can thus provide steric stabilization and prevent aggregation. Complexes formed with $DMA_{10}MPC_{30}$ were found to have a larger size (>200 nm) at high monomer nucleotide molar ratio. It was unlikely that agglomeration occurred as the complexes size was still significantly lower than that of DMA homopolymer. One of the possible explanations is that dissociation of complexes could have happened.

Figure 7:
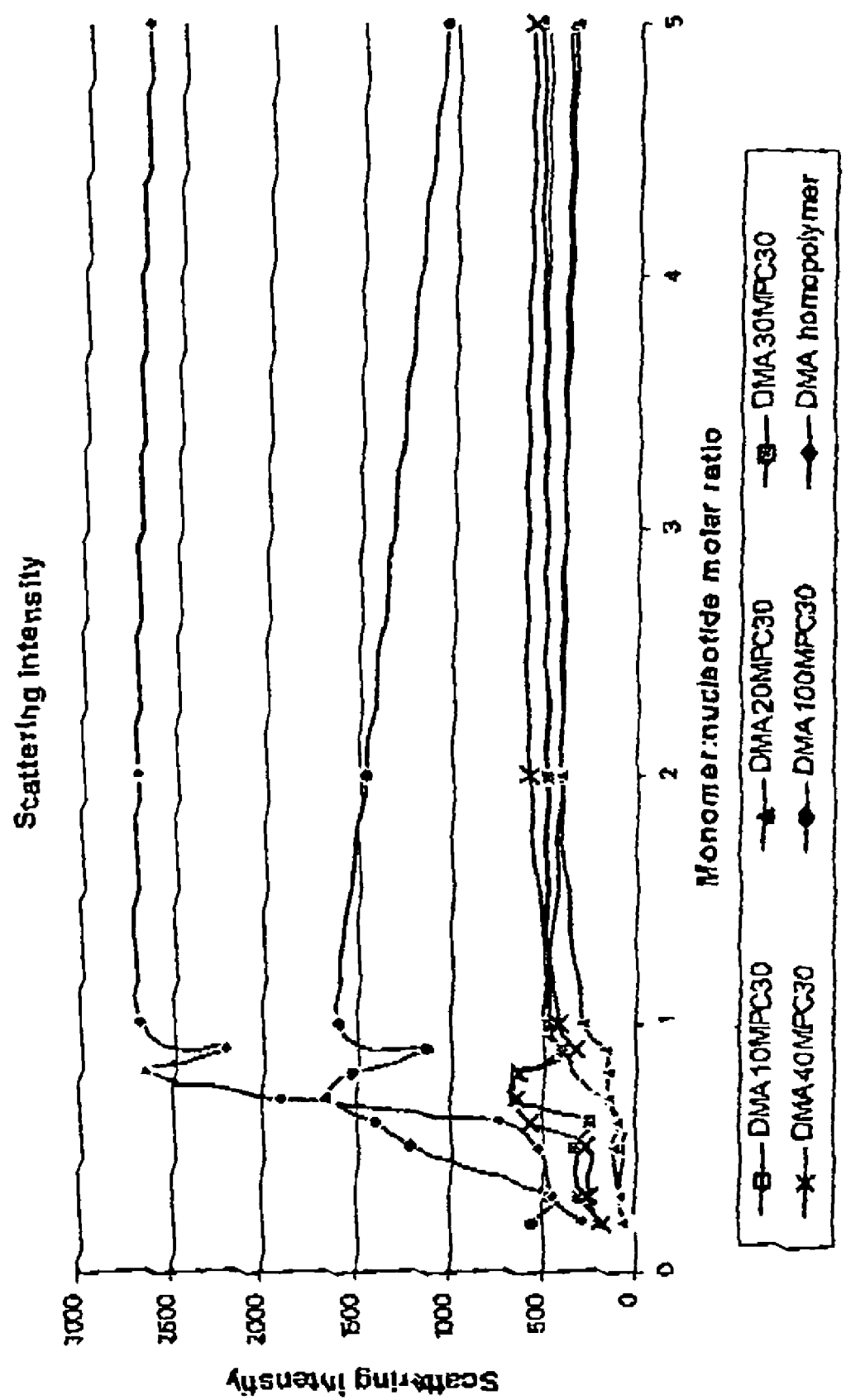

For complexes with a smaller proportion of DMA ($DMA_{10}MPC_{30}$ and $DMA_{20}MPC_{30}$), the scattering intensity was lower compared with those with a higher proportion of DMA, indicating that more complexes were formed (FIG. 7). The amount of complexes formed correlates to the proportion of DMA, which is responsible for the binding of DNA. It was also found that increasing the proportion of DMA results in uniform complex size, as the polydispersity decreased with longer DMA chain. For $DMA_{100}MPC_{30}$, the scattering intensity was significantly higher than other MPC-based copolymer although the complexes see was about the same, suggesting that either the complexes formed were very condensed or they were relatively insoluble.

TABLE 3

| Monomer:Nucleotide molar ratio | Paricle size ± SD (nm) (Polydispersity ± SD) Scattering Intensity ± SD | | |
|---|---|---|---|
| | $DMA_{10}MPC_{30}$ | $DMA_{30}MPC_{30}$ | $DMA_{100}MPC_{30}$ |
| 0.2 | 585.7 ± 50.1 (1.0 ± 0)<br>38.4 ± 2.8 | 275.1 ± 38.9 (0.884 ± 0.099)<br>184.0 ± 16.2 | 131.2 ± 12.1 (0.339 ± 0.164)<br>556.8 ± 261.4 |
| 0.5 | 151.0 ± 23.3 (0.645 ± 0.11)<br>67.5 ± 3.7 | 215.0 ± 0.4 (0.349 ± 0.011)<br>331.6 ± 10.0 | 149.1 ± 13.1 (0.238 ± 0.037)<br>1214.7 ± 186.1 |
| 0.7 | 101.5 ± 16.6 (0.748 ± 0.437)<br>186.4 ± 9.3 | 180.5 ± 0.9 (0.275 ± 0.008)<br>854.5 ± 2.3 | 147.9 ± 4.9 (0.172 ± 0.076)<br>1654.0 ± 168.9 |
| 0.8 | 157.2 ± 8.7 (0.514 + 0.030)<br>349.0 ± 16.8 | 197.4 ± 1.6 (0.284 ± 0.006)<br>651.8 ± 5.8 | 180.7 ± 19.1 (0.260 ± 0.029)<br>1526.6 ± 59.1 |
| 0.9 | 149.0 ± 7.2 (0.522 ± 0.032)<br>371.5 ± 15.4 | 167.1 ± 1.3 (0.362 ± 0.015)<br>407.2 ± 6.7 | 120.3 ± 0.3 (0.120 ± 0.029)<br>1122.0 ± 194.8 |

TABLE 3-continued

| Monomer:Nucleotide molar ratio | Particle size ± SD (nm) (Polydispersity ± SD) Scattering Intensity ± SD | | |
|---|---|---|---|
| | DMA$_{10}$MPC$_{30}$ | DMA$_{30}$MPC$_{30}$ | DMA$_{100}$MPC$_{30}$ |
| 1 | 294.4 ± 87.5 (0.877 ± 0.189) 508.6 ± 71.7 | 170.6 ± 2.7 0.325 ± 0.011 474.0 ± 4.5 | 130.1 ± 10.2 (0.170 ± 0.029) 1598.7 ± 658.7 |
| 2 | 202.4 ± 60.3 (0.700 ± 0.254) 418.0 ± 53.5 | 113.4 ± 2.1 (0.326 ± 0.047) 491.4 ± 13.9 | 141.0 ± 13.2 (0.220 ± 0.026) 1467.9 ± 61.9 |
| 3 | | 126.3 ± 8.1 (0.473 ± 0.078) 442.4 ± 14.4 | 106.9 ± 2.6 (0.189 ± 0.020) 813.1 ± 106.0 |
| 5 | 394.5 ± 159.3 (0.686 ± 0.236) 385.8 ± 45.6 | 148.3 ± 1.8 (0.418 ± 0.018) 550.8 ± 45.7 | 125.2 ± 9.0 (0.211 ± 0.008) 1052.1 ± 103.9 |
| 10 | 109.2 ± 6.9 (1.0 ± 0) 365.4 ± 11.7 | 169.9 ± 20.5 (0.525 ± 0.114) 539.7 ± 23.7 | 120.2 ± 12.2 (0.207 ± 0.005) 1004.3 ± 90.1 |

TABLE 4

| Monomer:Nucleotide molar ratio | Particle size ± SD (nm) (Polydispersity ± SD) Scattering intensity ± SD | | |
|---|---|---|---|
| | DMA Homopolymer | DMA40MPC10 | DMA40MPC30 |
| 0.2:1 | 226.0 ± 1.7 (0.403 ± 0.013) 292.3 ± 2.0 | 245.5 ± 27.2 (0.532 ± 0.194) 53.8 ± 0.6 | 174.9 ± 8.7 (0.499 ± 0.017) 70.4 ± 11.6 |
| 0.3:1 | 177.5 ± 8.1 (0.39 ± 0.064) 452.7 ± 11.3 | | 244.6 ± 17.1 (0.585 ± 0.049) 92.2 ± 7.0 |
| 0.5:1 | 167.5 ± 2.9 (0.376 ± 0.037) 527.2 ± 6.5 | 203.3 ± 8.7 (0.409 ± 0.044) 240.5 ± 6.1 | 249.9 ± 18.5 (0.679 ± 0.051) 130.0 ± 6.4 |
| 0.6:1 | 154.4 ± 2.1 (0.322 ± 0.024) 738.9 ± 11.0 | 259.9 ± 21.2 (0.337 ± 0.076) 263.1 ± 11.2 | 137.5 ± 2.6 (0.345 ± 0.019) 107.5 ± 5.6 |
| 0.7:1 | 195.6 ± 5.1 (0.304 ± 0.013) 1910.8 ± 23.1 | 290 ± 11.4 (0.258 ± 0.041) 192.3 ± 4.8 | 161.5 ± 4.6 (0.419 ± 0.028) 156.2 ± 9.0 |
| 0.8:1 | 540.4 ± 140.2 (0.459 ± 0.067) 2658.5 ± 24.7 | 320.9 ± 6.0 (0.326 ± 0.031) 145.8 ± 8.6 | 148.5 ± 2.4 (0.344 ± 0.007) 153.7 ± 14.0 |
| 0.9:1 | 1243.3 ± 107.4 (0.416 ± 0.031) 2225.5 ± 69.4 | 383.7 ± 16.1 (0.429 ± 0.014) 118.0 ± 1.7 | 154.5 ± 2.1 (0.373 ± 0.01) 172.5 ± 3.3 |
| 1.0:1 | 1704.0 ± 99.3 (0.691 ± 0.103) 2686.8 ± 69.0 | 411.7 ± 21.2 (0.482 ± 0.083) 105.7 ± 3.8 | 141.4 ± 1.7 (0.223 ± 0.005) 288.1 ± 5.5 |
| 2.0:1 | 1411.6 ± 172.1 (0.5 ± 0.036) 2714.4 ± 52.7 | 443.6 ± 22.7 (0.497 ± 0.047) 102.3 ± 5.0 | 127.2 ± 0.7 (0.299 ± 0.009) 415.6 ± 3.4 |
| 5.0:1 | 1436.7 ± 178.5 (0.568 ± 0.049) 2686.9 ± 39.7 | 527.8 ± 21.7 (0.433 ± 0.016) 102.4 ± 4.9 | 123.3 ± 0.009 (0.312 ± 0.009) 358.6 ± 3.7 |

The invention claimed is:

1. A composition comprising a block copolymer having an overall ionic charge and associated with the polymer a biologically active compound having a charge opposite that of the polymer and is characterised in that block copolymer comprises at least one zwitterionic block which has pendant zwitterionic groups and at least one ionic block which comprise ionic groups to confer said overall ionic charge, wherein the biologically active compound is anionic.

2. A composition according to claim 1 in which the active compound is a nucleic acid.

3. A composition according to claim 2 in which the nucleic acid is selected from the group consisting of oligo nucleotides, having 5 to 80 bases, single stranded RNA, single stranded DNA and double stranded DNA.

4. A composition according to claim 1 in which the biologically active compound is an anionic drug.

5. A composition according to claim 1 in which the biologically active compound and polymer are associated with one another in the form of particles having an average diameter less than 200 μm.

6. A composition according to claim 5 which is an aqueous composition in which the particles are suspended.

7. A composition according to claim 1 in which the zwitterionic block is formed from ethylenically unsaturated monomers including a zwitterionic monomer having the general formula

YBX  I in which Y is an ethylenically unsaturated group selected from the group consisting of $H_2C=CR-CO-A-$, $H_2C=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

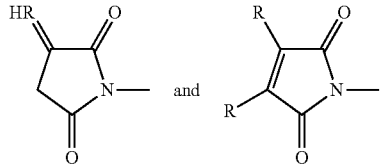

A is $-O-$ or $NR^1$;
$A^1$ is selected from the group consisting of a bond, $(CH_2)_lA^2$ and $(CH_2)_l\,SO_3-$ in which $l$ is 1 to 12;
$A^2$ is selected from the group consisting of a bond, $-O-$, $O-CO-$, $CO-O$, $CO-NR^1-$, $-NR^1-CO$, $O-CO-NR^1-$, and $NR^1-CO-O-$;
R is hydrogen or $C_{1-4}$ alkyl;
$R^1$ is hydrogen, $C_{1-4}$ alkyl or BX;

$R^2$ is hydrogen or $C_{1-4}$ alkyl;

B is selected from the group consisting of a bond, straight and branched alkanediyl groups, alkylene oxaalkylene groups, and alkylene (oligooxalkylene) groups, optionally containing one or more fluorine substituents; and X is a zwitterionic group.

8. A composition according to claim 7 in which X comprises a cation selected from the group consisting of ammonium, phosphonium and sulphonium groups and an anion selected from the group consisting of phosphate and phosphonate ester groups.

9. A composition according to claim 8 in which X has the general formula II

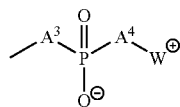

II in which the moieties $A^3$ and $A^4$, which are the same or different, are —O—, —S—, —NH— or a valence bond and $W^+$ is a group comprising an ammonium, phosphonium or sulphonium cationic group and a group linking the anionic and cationic moieties which is a $C_{1-12}$ alkanediyl group.

10. A composition according to claim 9 in which $W^+$ is a group of formula

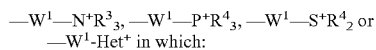

$W^1$ is selected from the group consisting of alkanediyl of 2-6 carbon atoms optionally containing one or more ethylenically unsaturated double or triple bonds, disubstituted-aryl (arylene), alkylene arylene, arylene alkylene, and alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same or different and each is selected from the group consisting of hydrogen, alkyl of 1 to 4 carbon atoms, and aryl or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; and Het is an aromatic nitrogen-, phosphorus- or sulphur-containing ring.

11. A composition according to claim 7 in which X has the general formula III

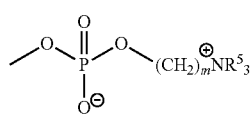

III where the groups $R^5$ are the same or different and each is hydrogen or $C_{1-4}$ alkyl, and m is from 1 to 4.

12. A composition according to claim 7 in which the ethylenic unsaturated group Y is $H_2C=CR-CO-A-$, in which R is hydrogen or methyl and A is NH or O.

13. A composition according to claim 7 in which the zwitterionic monomer is 2-methacryloyloxyethyl-2'-trimethylammonium ethyl phosphate inner salt.

14. A composition according to claim 7 in which the ethylenically unsaturated monomers include comonomer.

15. A composition according to claim 14 in which the comonomer has the general formula IX

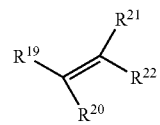

IX in which $R^{19}$ is selected from the group consisting of hydrogen, halogen, $C_{1-4}$ alkyl and groups $COOR^{23}$ in which $R^{23}$ is hydrogen and $C_{1-4}$ alkyl;

$R^{20}$ is selected from the group consisting of hydrogen, halogen and $C_{1-4}$ alkyl;

$R^{21}$ is selected from the group consisting of hydrogen, halogen, $C_{1-4}$ alkyl and groups $COOR^{23}$ provided that $R^{19}$ and $R^{21}$ are not both $COOR^{23}$; and $R^{22}$ is selected from the group consisting of $C_{1-10}$ alkyl, a $C_{1-20}$ alkoxycarbonyl, a mono- or di-($C_{1-20}$ alkyl) amino carbonyl, a $C_{6-20}$ aryl, $C_{7-20}$ aralkyl, $C_{6-20}$ aryloxycarbonyl, $C_{1-20}$-aralkyloxycarbonyl, $C_{6-20}$ arylamino carbonyl, $C_{7-20}$ aralkyl-amino, hydroxyl and $C_{2-10}$ acyloxy groups, any of which may have one or more substituents selected from the group consisting of halogen atoms, alkoxy, oligo-alkoxy, aryloxy, acyloxy, acylamino, amine, carboxyl, sulphonyl, phosphoryl, phosphino, zwitterionic, hydroxyl, vinyloxycarbonyl, and reactive silyl and silyloxy groups;

or $R^{22}$ and $R^{21}$ or $R^{22}$ and $R^{20}$ may together form —$CONR^{24}CO$ in which $R^{24}$ is a $C_{1-20}$ alkyl group.

16. A composition according to claim 1 in which the ionic block is formed of ethylenically unsaturated monomers including an ionic monomer of general formula VI $Y^1B^1Q$     VI in which $Y^1$ is selected from the group consisting of $H_2C=CR^{14}-CO-A^8-$, $H_2C=CR^{14}-C_6H_4-A^9-$, $H_2C=CR^{14}-CH_2A^{10}$, $R^{16}O-CO-CR^{14}=CR^{14}-CO-O$, $R^{14}CH=CH-CO-O-$, $R^{14}CH=C(COOR^{16})CH_2-CO-O$,

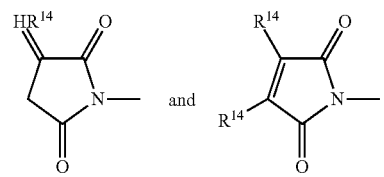

$A^8$ is —O— or $NR^{15}$;

$A^9$ is selected from the group consisting of a bond, $(CH_2)_qA^{10}$ and $(CH_2)_q SO_3$— in which q is 1 to 12;

$A^{10}$ is selected from the group consisting of a bond, —O—, O—CO—, CO—O, CO—$NR^{15}$—, —$NR^{15}$—CO, O—CO—$NR^{15}$, and $NR^{15}$—CO—O—;

$R^{14}$ is hydrogen or $C_{1-4}$ alkyl;

$R^{15}$ is hydrogen, $C_{1-4}$ alkyl or $B^1Q$;

$R^{16}$ is hydrogen or $C_{1-4}$ alkyl;

$B^1$ is selected from the group consisting of a bond, straight and branched alkanediyl groups, alkylene oxaalkylene groups and alkylene (oligooxalkylene) groups, optionally containing one or more fluorine substituents; and Q is an ionic or ionisable moiety.

17. A composition according to claim 16 in which Q is selected from groups having the formula $-NR^{17}{}_p$, $-PR^{17}{}_p$ and $SR^{17}{}_r$, in which p is 2 or 3, r is 1 or 2, the groups $R^{17}$ are the same or different and each is selected from the group consisting of hydrogen, $C_{1-24}$ alkyl and aryl, or two of the groups $R^{17}$ together with the heteroatom to which they are attached form a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{17}$ groups may be substituted by amino or hydroxyl groups or halogen atoms.

18. A composition according to claim 17 in which Q is $-NR^{17}{}_2$ where each $R^{17}$ is the same and is $C_{1-12}$-alkyl.

19. A composition according to claim 16 in which $B^1$ is a $C_{2-6\text{-}alkanediyl}$.

20. A composition according to claim 16 in which the ethylenically unsaturated monomers include a comonomer.

21. A composition according to claim 20 in which the comonomer has the general formula IX

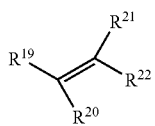

IX in which $R^{19}$ is selected from the group consisting of hydrogen, halogen, $C_{1-4}$ alkyl and groups $COOR^{23}$ in which $R^{23}$ is hydrogen or $C_{1-4}$ alkyl;

$R^{20}$ is selected from the group consisting of hydrogen, halogen and $C_{1-4}$ alkyl;

$R^{21}$ is selected from the group consisting of hydrogen, halogen, $C_{1-4}$ alkyl and groups $COOR^{23}$ provided that $R^{19}$ and $R^{21}$ are not both $COOR^{23}$; and $R^{22}$ is selected from the group consisting of $C_{1-10}$ alkyl, a $C_{1-20}$ alkoxycarbonyl, mono- and di-($C_{1-20}$ alkyl) amino carbonyl, $C_{6-20}$ aryl, $C_{7-20}$ aralkyl, $C_{6-20}$ aryloxycarbonyl, $C_{1-20}$-aralkyloxycarbonyl, $C_{6-20}$ arylamino carbonyl, $C_{7-20}$ aralkyl-amino, hydroxyl and $C_{2-10}$ acyloxy groups, any of which may have one or more substituents selected from the group consisting of halogen atoms, alkoxy, oligo-alkoxy, aryloxy, acyloxy, acylamino, amine, carboxyl, sulphonyl, phosphoryl, phosphino, zwitterionic, hydroxyl, vinyloxycarbonyl and reactive silyl and silyloxy groups;

or $R^{22}$ and $R^{21}$ or $R^{22}$ and $R^{20}$ may together form $-CONR^{24}CO$ in which $R^{24}$ is a $C_{1-20}$ alkyl group.

22. A composition according to claim 1 in which at least one of the blocks has a polydispersity of molecular weight less than 2.0.

23. A composition according to claim 1 in which the degree of polymerisation of the ionic block is in the range 5 to 2000 and the degree of polymerisation of the zwitterionic block is in the range 2 to 1000 and in which the ratio of the degrees of polymerisation of the ionic block to the zwitterionic block is in the range 1:5 to 10:1.

24. A composition according to claim 23 in which the degree of polymerisation of the ionic block is in the range 10 to 250, the degree of polymerisation of the zwitterionic block is in the range 5 to 100 and the ratio of the degrees of polymerisation of the ionic block to the zwitterionic block is in the range 1:1 to 5:1.

25. A composition according to claim 1 in which at least one of the blocks is formed by a living radical polymerisation process.

26. A composition according to claim 25 in which the living radical polymerisation process is a group or atom transfer polymerisation process.

27. A composition according to claim 1 in which the relative amounts of biologically active compound and polymer are in the range 1:5 to 10:1 based on equivalents of the polymer to active compound charged groups.

28. A composition according to claim 27 in which the said relative amounts are in the range 1:2 to 5:2.

29. A composition according to claim 1 in which the biologically active compound is polyanionic.

30. A composition comprising a block copolymer having an overall ionic charge and associated with the polymer a biologically active compound having a charge opposite that of the polymer wherein the block copolymer comprises at least one zwitterionic block which has pendant zwitterionic groups and at least one ionic block which comprise ionic groups to confer said overall charge, wherein the biologically active compound is anionic and wherein the ionic block is formed of ethylenically unsaturated monomers including an ionic monomer of general formula VI:

$$Y^1B^1Q \qquad \qquad VI$$

in which $Y^1$ is selected from the group consisting of $H_2C=CR^{14}-CO-A^8-$, $H_2C=CR^{14}-C_6H_4-A^9-$, $H_2C=CR^{14}-CH_2A^{10}$, $R^{16}O-CO-CR^{14}=CR^{14}-CO-O$, $R^{14}CH=CH-CO-O-$, $R^{14}CH=C(COOR^{16})CH_2-CO-O$,

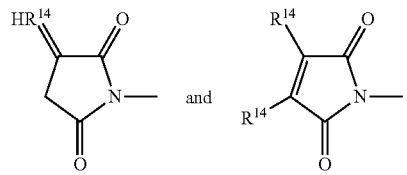

$A^8$ is $-O-$ or $NR^{15}$;

$A^9$ is selected from the group consisting of a bond, $(CH_2)_qA^{10}$ and $(CH_2)_q SO_3-$ in which q is 1 to 12;

$A^{10}$ is selected from the group consisting of a bond, $-O-$, $O-CO-$, $CO-O$, $CO-NR^{15}-$, $-NR^{15}-CO$, $O-CO-NR^{15}-$, and $NR^{15}-CO-O-$;

$R^{14}$ is hydrogen or $C_{1-4}$ alkyl;

$R^{15}$ is hydrogen, $C_{1-4}$ alkyl or $B^1Q$;

$R^{16}$ is hydrogen or $C_{1-4}$ alkyl;

$B^1$ is selected from the group consisting of a bond, straight and branched alkanediyl groups, alkylene oxaalkylene groups, and alkylene (oligooxalkylene) groups, optionally containing one or more fluorine substituents; and Q is $-NR^{17}{}_2$ where each $R^{17}$ is the same and is $C_{1-12}$ alkyl.

* * * * *

UNITED STATES PATENT AND TRADEMARK OFFICE
CERTIFICATE OF CORRECTION

PATENT NO. : 8,182,802 B2
APPLICATION NO. : 10/506814
DATED : May 22, 2012
INVENTOR(S) : Andrew Lennard Lewis et al.

It is certified that error appears in the above-identified patent and that said Letters Patent is hereby corrected as shown below:

Title Page 1, item 57 in the Abstract, line 1: delete "a" (first occurrence); line 5, change "diablock" to --diblock--; lines 11-12, change "2-methacyloyloxy-etyl-2$^1$-trimethyl ammonium ethyl phosphate liner salt" to --2-methacryloyloxyethyl-2'-trimethyl ammonium ethyl phosphate inner salt--

Column 1, line 25: change "from" to --form--

Column 1, line 29: change "so called" to --so-called--

Column 1, lines 34-35: change "Pack," to --(Pack,-- and "217." to --217).--

Column 1, line 39: delete "the level of" and change "in" to --of--

Column 1, line 52: change "that" to --at--

Column 2, line 29: change "(2000)" to --(2000),--

Column 9, line 23: change "polylispersity" to --polydispersity--

Column 10, line 63: change "$W_{3+}$," to --$W^{3+}$--

Column 11, line 64: change "an" to --on--

Column 13, line 66: change "active attract" to --active compound attract--

Column 14, line 34: change "biologically" to --biological--

Column 15, Table 1 header: change "DEAEMA" to --DEA--

Column 15, line 34: change "Institution." to --Institution--

Signed and Sealed this
Nineteenth Day of February, 2013

Teresa Stanek Rea
*Acting Director of the United States Patent and Trademark Office*

CERTIFICATE OF CORRECTION (continued)

Column 15, line 36: delete "is"

Column 16, line 35: change "standards." to --standards).--

Column 17, line 39: change "MPC20-DMA20" to --MPC$_{20}$DMA$_{20}$--

Column 17, line 45: change "fluoresce" to --fluorescent-- and "(ethydium" to --(ethidium--

Column 17, lines 56 and 57: change "MPC20-DMA20" to --MPC$_{20}$DMA$_{20}$--

Column 18, line 47: change "MPC30-DMA30" to --MPC$_{30}$DMA$_{30}$--

Column 18, line 49: change "polyolispersity" to --polydispersity--

Column 18, line 62: change "PLD" to --PhD--

Column 18, line 64: change "DMA-OEGMA15" to --DMA-OEGMA$_{15}$--

Column 18, line 66: change "DMA-OEGMA7" to --DMA-OEGMA$_7$--

Column 19, line 14: change "DMAx-MPC30" to --DMA$_x$-MPC$_{30}$--

Column 19, line 32: change "DMA40MPCX" to --DMA$_{40}$-MPC$_x$--

Column 19, line 48: change "25° C." to --25° C--

Column 20, line 23: change "MPC30 DMAX" to --MPC$_{30}$-DMA$_x$--

Column 20, line 24: change "MPCX-DMA 40" to --MPC$_x$-DMA$_{40}$--

Column 25, line 25, Claim 19: change "C$_{2\text{-}6\text{-}alkanediyl}$" to --C$_{2\text{-}6}$-alkanediyl--

Column 25, line 54, Claim 21: change "suiphonyl" to --sulphonyl--